United States Patent [19]
Rogers et al.

[11] Patent Number: 5,672,830
[45] Date of Patent: Sep. 30, 1997

[54] MEASURING ANISOTROPIC MECHANICAL PROPERTIES OF THIN FILMS

[75] Inventors: John A. Rogers, Castle Rock, Colo.; Keith A. Nelson, Newton, Mass.; Lisa Dhar, Northbrook, Ill.

[73] Assignee: Massachusetts Institute of Technology, Cambridge, Mass.

[21] Appl. No.: 763,873

[22] Filed: Dec. 11, 1996

Related U.S. Application Data

[63] Continuation of Ser. No. 318,021, Oct. 4, 1994, abandoned.
[51] Int. Cl.⁶ .................................................. G01N 29/18
[52] U.S. Cl. ........................... 73/597; 73/643; 356/432 T
[58] Field of Search ............................ 73/597, 598, 602, 73/643, 655; 356/432 T, 354

[56] References Cited

U.S. PATENT DOCUMENTS 4,710,030  12/1987  Tauc et al. ................................. 73/643
4,728,165   3/1988  Powell et al. ............................. 350/364

OTHER PUBLICATIONS

Barish et al., "Photoinduced ionization of bovine serum albumin by holographic relaxation methods[a)]", J. Chem. Phys., 85:4194–4195, 1986.

Burzynski et al., "Study of anisotrophy of acoustic wave propagation in stretched poly(vinylidene difluoride) film using the picosecond transient grating technique," Polymer, 30:1247–1250, 1989.

Deeg et al., "New Grating Experiments in the Study of Irreversible Photochemical Reactions," IEEE J. Quantum Electronics, QE-22:1476–1481, 1986.

Espinet et al., "Laser–induced gratings in nematic/cholesteric mixtures," App. Phys. Letters, 50:1924–1926, 1987.

Fishman et al., "Surface Selectivity in Holographic Transient Grading–Diffraction." (submitted for publication).

Greene et al., "Picosecond Relaxation Dynamics in Polydiacetylene–pTs, Chem. Phys. Letters," 139:381–385, 1987.

Meth et al., "Experimental and theoretical analysis of transient grating generation and detection of acoustic waveguide modes in ultrathin solids," J. App. Phys., 67:3362–3377, 1990.

Meth et al., "Generation and Detection of Acoustic Waveguide Modes in Ultrathin Crystals Using The Transient Grating Technique," Chem. Phys. Letters, 162:306–312, 1989.

Nelson et al., "Optical generation of tunable ultrasonic waves," J. App. Phys., 53:1144–1149, 1982.

Nizzoli, "Problems with the determination of elastic constants from higher–order surface waves: Results for Al on NaCl," Physical Review B, 37:1007–1010, 1988.

Noll et al., "Picosecond Photoinduced Index Changes in a–Si:H and Related Alloys Measured by Transient Grating Experiments," J. Non–Crystalline Solids, 97 & 98:141–144, 1987.

Portella et al., "Four–Wave Mixing Experiments in Cresyl Violet Thin Films: Inadequacy of a Two–Level Interpretation," J. Phys. Chem., 91:3715–3719, 1987.

Prasad, "Non–Linear Optical Effects in Thin Organic Polymeric Films," Thin Solid Films, 152:275–294, 1987.

Rao et al., "Third order nonlinear optical interactions in thin films of poly–p–phenylenebenzobisthiazole polymer investigated by picosecond and subpicosend degenerate four wave mixing" App. Phys. Letters, 48:1187–1189, 1986.

Rao et al., "Picosecond transient grating studies of polymeric thin films," App. Phys. Letters, 48:387–389, 1986.

(List continued on next page.)

*Primary Examiner*—John E. Chapman
*Attorney, Agent, or Firm*—Fish & Richardson P.C.

[57] ABSTRACT

Anisotropic mechanical properties of thin films are measured by exciting time-dependent waveguide acoustic modes in the thin film sample with a pair of excitation pulses from an excitation laser. The waveguide acoustic modes are then optically detected by diffracting a probe laser beam off the excited modes. The probe beam is detected to generate an electronic signal. The anisotropic moduli and related properties in the film are determined by analyzing the electronic signal using a mathematical inversion procedure.

18 Claims, 7 Drawing Sheets

OTHER PUBLICATIONS

Rao et al., "Picosecond Laser-Induced Transient Grating Probe of the Mechanical Properties of High-Modulus Poly(p-phenylenebenzobisoxazole-2,6-diyl)", Macromolecules, 22:985-989, 1989.

Rose et al., "Picosecond Transient Grating Transport in Anthracene Single Crystals," Measurements of Singlet Excitation, Chem. Phys. Leters, 106:13-19, 1984.

Rothenhäusler, "Plasmon Surface Polariton Fields for the Characterization of Thin Films*," Thin Solid Films, 159:323-330, 1988.

A.R. Duggal et al., "Real-time characterization of acoustic modes of polyimide thin-film coatings using impulsive stimulated thermal scattering," App. Phys. Lett. 60(6) 10 Feb. 1992, pp. 692-694.

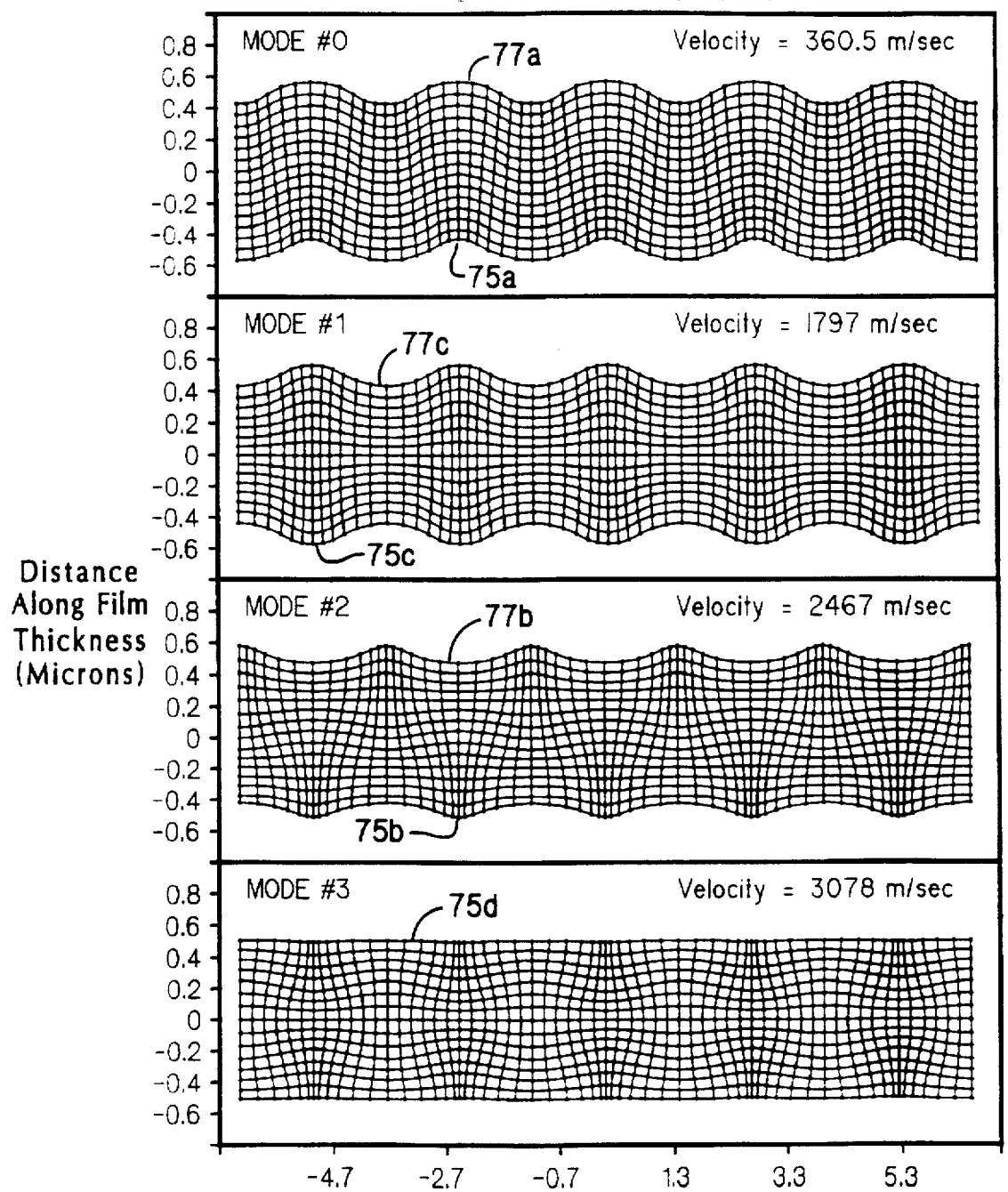
FIG. 3A Distance along the Grating in Microns

MEASURING ANISOTROPIC MECHANICAL PROPERTIES OF THIN FILMS

This application is a continuation of Ser. No. 08/318,021 filed Oct. 4, 1994, now abandoned.

This invention was made with government support under grant Number 9317198-DMR awarded by the National Science Foundation. The government has certain rights in the invention.

FIELD OF THE INVENTION

This invention relates to analyzing thin films so that anisotropic properties can be measured.

BACKGROUND

Thin metal, polymer, and semiconductor films are common in microelectronic, optical, biomedical, and aerospace devices. The mechanical properties of these films along the in-plane and out-of-plane dimensions may be different, or anisotropic, because of chemical or gross structural differences in the film. These anisotropic properties can affect the performance of the films and the devices incorporating them.

Polyimide films, for example, which are used to coat silicon wafers, may have transverse isotropic symmetry, especially when spin cast. This symmetry is attributed to a preferential ordering of the polyimide chains in the plane of the film and has been inferred from significant differences between in and out-of-plane indices of refraction, large differences between the in and out-of-plane thermal expansion coefficients, anisotropy in fluid transport properties, and, most directly, from x-ray diffraction measurements. The anisotropy of the mechanical moduli has not been measured in thin polyimide films, but it is expected that ordering of the polymer chains would give rise to in-plane moduli which are larger than the out-of-plane moduli because there is more covalent (i.e., stronger) bonding along in the plane, rather than out of the plane of the film. Anisotropies in the moduli of elasticity may also be present in other types of films, such as other polymer films and in sputter-deposited metal films.

Optical measurement techniques have been used to characterize the mechanical properties of thin films. In general, these techniques fall into two categories: laser-based ultrasonic methods and techniques involving the measurement of spontaneous Brillouin scattering. Two laser-based ultrasonic methods, Impulsive Stimulated Thermal Scattering (ISTS) and Impulsive Stimulated Brillouin Scattering (ISBS), use laser light to excite films. In the ISTS technique, two time-coincident laser pulses are overlapped in the film, creating an optical interference pattern. The optical energy is then absorbed by the sample at the peaks (i.e., the regions of constructive interference) of the pattern, resulting in deposition of heat in the film, which is followed by thermal expansion of the irradiated regions, and the launching of coherent, counter-propagating ultrasonic phonons whose wavelength and orientation match the interference pattern geometry.

In ISBS, the sample is also excited using optical energy, but with radiation that is not absorbed by the film. In this case, optical energy is coupled directly into the film's acoustic field to excite the acoustic processes. This process takes advantage of the inherent spectral line width in 100-picosecond (ps) excitation pulses. Higher-frequency photons from each excitation pulse are annihilated to create lower-frequency photons in the opposite excitation pulse. Acoustic phonons of the difference frequency and wavevector are then generated in the medium, resulting in the production of counter-propagating phonons along the in-plane dimension of the film.

In both ISTS and ISBS, the phonon propagation continues after the excitation pulses leave the sample, causing a time-dependent, spatially periodic variation in the material density. The phonons can be detected by directing a probe beam onto the film because the relevant optical properties (i.e., the real and imaginary parts of the index of refraction) are density-dependent. The excited region of the sample functions as a transient diffraction grating, resulting in diffraction and modulation of the incident probe beam. Mechanical properties can be characterized by analyzing the diffracted probe beam.

Spontaneous Brillouin scattering measurements, the other category of optical measurement techniques, do not involve direct optical excitation of the acoustic modes. In these methods, the sample is monitored with a probe laser to detect acoustic modes that are present because of the temperature of the film. Typically, data collection takes at least several minutes for thin (i.e., 1–10 micron) films. Attempts to measure the anisotropic moduli of superlattices and films using Brillouin scattering have been reported in the literature.

SUMMARY

This invention is directed to rapid, accurate measurement of the anisotropic mechanical properties of thin films using lasers to optically excite the films.

In general, in one aspect, the invention provides a method for determining the anisotropic properties of a thin sample. The method includes the steps of exciting time-dependent waveguide acoustic modes in the sample by directing two time-coincident laser pulses onto the sample so that they overlap in an excitation region and interfere to form an excitation field having a known wavevector, and then detecting the waveguide acoustic modes by directing a probe beam onto the excitation region so that it is diffracted, with the probe beam having a temporal width that is comparable to the detectable presence of the time-dependent waveguide mode. The diffracted probe beam is analyzed to determine the measured phase velocities of the waveguide acoustic modes. The anisotropic properties of the sample are determined by proposing stiffness tensors in directions of interest; calculating phase velocities based on the proposed stiffness tensors; comparing the calculated phase velocities to the measured phase velocities; repeating the proposing, calculating, and comparing steps until the calculated phase velocities match the measured phase velocities to a desired degree; and, determining the anisotropic properties in direction of interest from the stiffness tensors for which the calculated phase velocities match the measured phase velocities to the desired degree.

In preferred embodiments, the probe beam has a small dimension compared to the excitation region, and the equations of motion for the sample are described by $$p\frac{\partial^2 u_i}{\partial t^2} - c_{ijkl}\frac{\partial^2 u_k}{\partial x_j \partial x_l} = 0$$

where p is the density, μ is the displacement, and c is the the stiffness tensor, and the coordinate system is defined with the wavevector in the z direction. The excitation pulses are preferably cylindrically focused to form an elliptical spot, with the major axis of the elliptical spot being in the z direction, and the probe pulse has a dimension of about an order of magnitude smaller than the excitation region. In other preferred embodiments, the laser pulses are selected to maximize the number of waveguide modes excited in the sample by having a wavelength at which the sample is about 20–80% absorbant, and the wavevector-thickness product is between about 2–6.

Preferably, the probe beam has a square temporal profile, and is generated by temporally modulating an output of a cw laser.

In other embodiments, the method additionally includes the step of comparing the determined anisotropic material properties of the film with at least one previously determined property to allow the quality of the film to be monitored. Preferably, the anisotropic property is a sound velocity.

In another aspect, the invention provides a method for determining the anisotropic properties of a thin sample. The method includes the steps of exciting time-dependent waveguide acoustic modes in the sample by directing two time-coincident laser pulses onto the sample so that they overlap in an excitation region and interfere to form an excitation field having a known wavevector; detecting the waveguide acoustic modes by directing a probe beam onto the excitation region so that it is diffracted, with the probe beam having a temporal width that is comparable to the detectable presence of the time-dependent waveguide mode; and analyzing the diffracted probe beam to determine a measured phase velocity or frequency of the waveguide acoustic modes, thereby allowing the anisotropic properties of the sample to be determined.

The inventions have many advantages. In this technique, the optical excitation of the films induces waveguide modes in the film. These modes are coherent acoustic phonons having wavelengths on the order of the film thickness which propagate along the film surface and involve shear and longitudinal motions both in and out of the plane of the film. The waveguide modes are detected using a diffracted probe beam to produce a light-induced signal. Analysis of this signal allows the phase velocity dispersion of the waveguide modes to be determined. This data is then analyzed using a mathematical inversion procedure to determine the anisotropic moduli in the film. The data can be collected in a matter of seconds with a high signal-to-noise ratio, making the measurements of anisotropic moduli rapid and highly accurate.

Because the film measurement method is both fast and accurate it can be used, for example, on-line during semiconductor wafer processing to determine the anisotropic sound speeds in polymer films. This property, when measured during processing, is then used as a criteria to reject devices which include films having unacceptable material properties. Similarly, film formation processes, such as the curing of polymer films, can be monitored by measuring the sound speeds in the curing films. When implemented in this fashion, the method may be used in combination with a process controller to make real-time modifications to fabrication processes, thereby allowing production of higher-quality films. Another advantage of the technique is that it can be used to measure anisotropic properties when the films are at low temperatures.

Other features, aspects, and advantages follow.

BRIEF DESCRIPTION OF THE DRAWINGS

FIGS. 3A–3C are, respectively, grid-distortion diagrams of the four lowest waveguide modes in a polyimide film when the wavevector-thickness product is 2.5, a grid-distortion diagram of the lowest-order waveguide mode, and a grid-distortion diagram showing the in and out-of-plane motions in the film;

DETAILED DESCRIPTION

Figure 1:
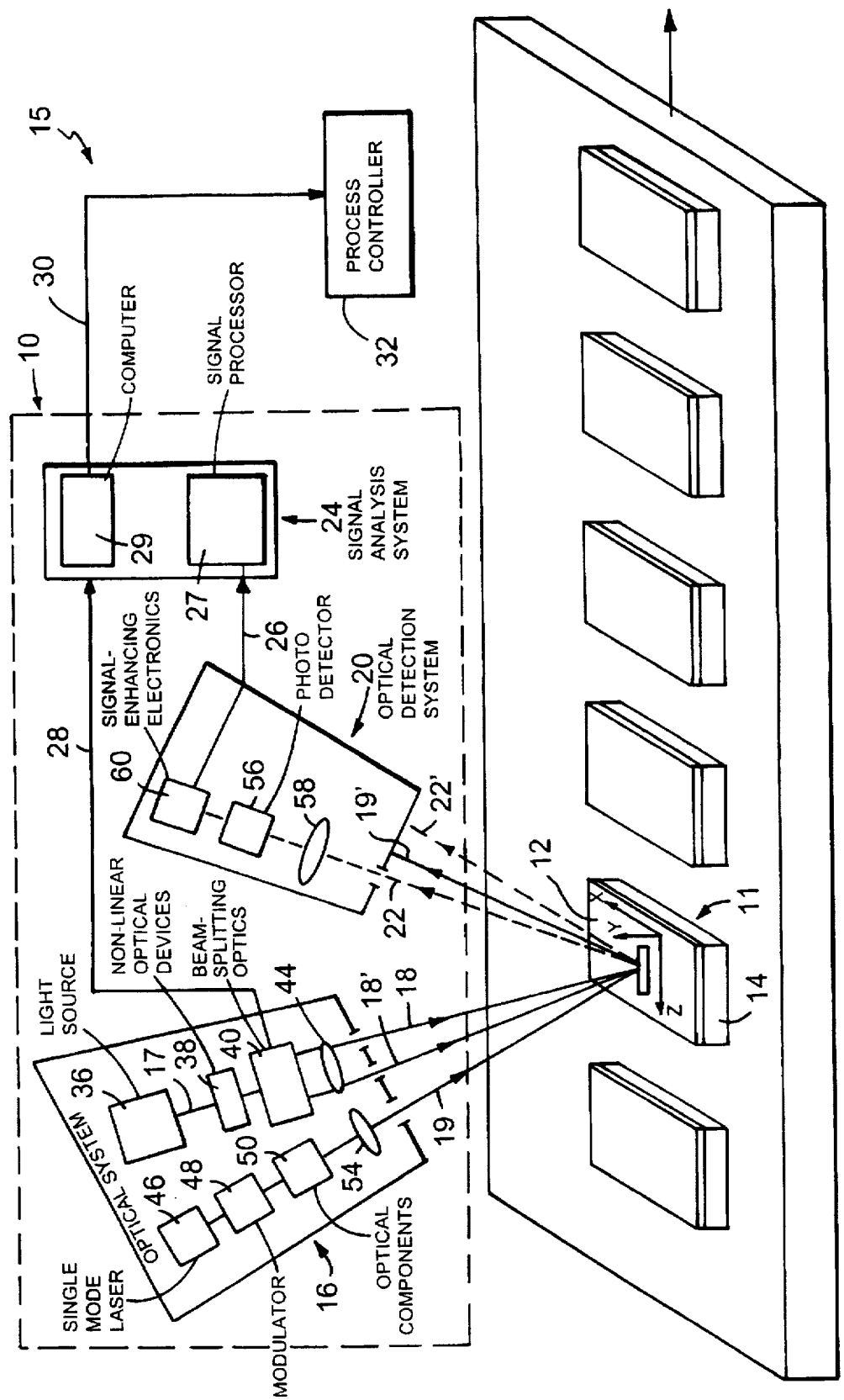
FIG. 1 is a schematic of a film-measuring device implemented in a device assembly line.

Referring first to FIG. 1, an assembly line 15 for processing a series of film-containing devices 11 includes a film-measuring device 10 that allows the anisotropic mechanical properties of a thin film 12 adhered to the substrate 14 of the device 11 to be accurately determined in a rapid, non-invasive manner. The film-measuring device 10 includes an optical system 16 for generating and directing excitation 18, 18' and probe 19 beams toward the surface of the film. A spatially periodic, time-dependent optical intensity pattern, caused by optical interference between the excitation beams in the film, excites coherent waveguide modes. The probe beam 19 is then used to irradiate the excited region on the film surface. A diffracted portion 22 (or, alternatively, portion 22') of the probe beam 19 is detected using an optical detection system 20. The detection system 20 generates a light-induced signal 26, which is then input with a wavevector signal 28 (indicating the wavevector of the excited waveguide modes) to a signal-analysis system 24 containing a signal processor 27 and a computer 29.

The wavevector 28 and light-induced 26 signals are analyzed to determine the phase velocities of the waveguide modes. These measured phase velocities are then compared to calculated phase velocities by an iterative mathematical procedure (described below) to determine the anisotropic material properties of the film 12. A status signal 30 indicating these properties is then generated and input to a process controller 32, which processes the signal 30 to determine the quality of the film. Upon analysis of the anisotropic information, the system, for example, may then reject the film-containing device 11 due to poor quality of the film 12.

The optical system for directing the excitation and probe beams is constructed so that the measurement of anisotropic properties can be made with high accuracy to distinguish acceptable films from those that are unacceptable during the short time window permitted by the assembly line. In particular, waveguide modes are preferably detected using a probe beam with a temporal width that is comparable to or longer than the detectable presence of the waveguide modes in the film. This produces a signal having a high signal-to-noise ratio (greater, for example, than 100:1) which is generated in a short period of time (e.g., on the order of a millisecond). The signal-to-noise ratio can be further enhanced by signal averaging. The signal averaging rate is limited only by the repetition rate of the laser (typically around 1 kHz) or the speed of the recording electronics. By signal averaging, the signal-to-noise ratio can be improved to greater than 500:1 while still keeping collection times in the range of about 1 second.

The excitation system is also arranged to maximize the number of waveguide modes that are excited in the film by each laser pulse so that the accuracy is increased and analysis time is shortened. In particular, the excitation pulses have a short time duration relative to the waveguide mode oscillation period, which is typically on the order of picoseconds to nanoseconds. In addition, the excitation pulses preferably have a wavelength at which 50% of the light is absorbed by the film. If the absorption is too large, such that all of the light is absorbed in the first 10–20 nm of the film, the excitation will be limited only to modes localized to the surface. Similarly, a larger number of modes can be excited by using higher wavevectors. Typically, the wavevector-thickness product is in the range of 2–6.

The probe beam is focussed to a spot size that is smaller than the excitation beams. In particular, the excitation beams are preferably cylindrically focused to produce an elliptical spot on the film so that the major axis of the ellipse is along the direction of the wavevector and is much larger than the fringe spacing of the grating. As will be discussed in more detail below, this arrangement permits the computation of anisotropic properties to be simplified without substantially reducing accuracy, which results in a faster, more reliable analysis.

The anisotropic properties are determined by an iterative fitting procedure in which the phase velocities measured by the optical system are compared to calculated phase velocities. The calculated phase velocities are determined by proposing values of stiffness tensor components in the directions of interest. The correct stiffness tensor components are found when the calculated phase velocities match the measured phase velocities to a desired degree.

The equations of motion used in the calculation are derived starting with the acoustic field equations which generally govern material motion as described in M. Grimsditch et. al, Phys. Rev. Lett. 58:1216 (1987). The general differential equation is:

$$p \frac{\partial^2 u_j}{\partial t^2} - c_{ijkl} \frac{\partial^2 u_k}{\partial x_j \partial x_l} = 0$$

where $\rho$ is the density, u is the displacement, and c is the stiffness tensor.

In this analysis, the coordinate system is defined such that the wavevector points in the z direction (direction index 3). Next, the x and z directions (directions 1 and 3, respectively) are assumed to extend infinitely. These conditions are valid experimentally. As discussed above, the excitation beams are cylindrically focused to produce an elliptical spot such that the major axis of the focus is much longer than the fringe spacing, which allows the motions in the z direction to be assumed to be purely sinusoidal. Moreover, the probe beam size is small compared to that of the excitation beam. The derivatives along x can thus be ignored. The equations of motion then can be simplified to:

$$p \frac{\partial^2 u_y}{\partial t^2} - c_{11} \frac{\partial^2 u_z}{\partial y^2} - c_{44} \frac{\partial^2 u_z}{\partial z^2} - (c_{23}+c_{44}) \frac{\partial^2 u_z}{\partial y \partial z} = 0$$

$$p \frac{\partial^2 u_y}{\partial t^2} - c_{44} \frac{\partial^2 u_z}{\partial y^2} - c_{11} \frac{\partial^2 u_z}{\partial z^2} - (c_{23}+c_{44}) \frac{\partial^2 u_z}{\partial y \partial z} = 0$$

where the c's are elements of the stiffness tensor. This expression can be written in tensor matrix form:

$$c_{ij} = \begin{bmatrix} c_{11} & c_{12} & c_{13} & 0 & 0 & 0 \\ c_{12} & c_{22} & c_{13} & 0 & 0 & 0 \\ c_{13} & c_{13} & c_{22} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & \frac{1}{2}(c_{11}-c_{22}) \end{bmatrix}$$

The elements of the tensor are determined by initially proposing a series of values for the stiffness tensor elements and then calculating the waveguide mode phase velocities by finding the position of zeroes in a 6×6 determinant which is a function of only the wavevector-thickness product. The specific form of this determinant is given in the computer codes provided in Appendix A (unsupported films) and Appendix B (supported films). The determinant is defined by imposing the appropriate boundary conditions at the two film interfaces, and performing a Laplace transform of the determinant along t, a Fourier transform along z, and postulating solutions to $u_y$ and $u_z$ of the form ~exp(iqby), where b is unknown. The process is repeated iteratively by adjusting the tensor elements and using a non-linear least squares fitting algorithm, such as a Marquardt-Levenburg algorithm to fit the data. The resulting set of tensor elements are compared to standard data to determine the quality of the film.

The tensor elements can also be used to calculate the anisotropic sound velocities in the film. In the case of an unsupported film, the boundary conditions of the air-film interface require continuity in the transient displacements and stresses. In the case of supported films, the boundary conditions must be modified to account for tight binding to a substrate by requiring continuity of stresses and displacements of the interface. In addition, the thickness may be determined along with the anisotropic material properties during the data analysis steps by treating this property as an additional unknown parameter. The code included in the appendices has the capability of determining the film thickness. Further, mode frequency rather than phase velocity can be used in the fitting procedure.

Figure 3B:
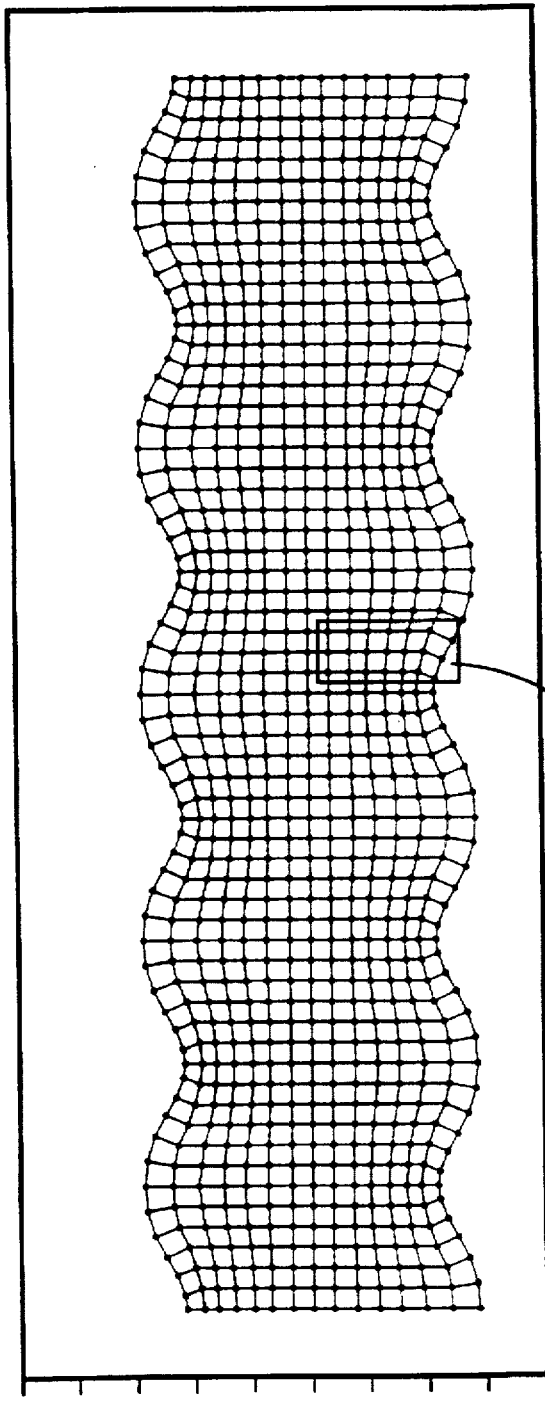
Figure 3C:
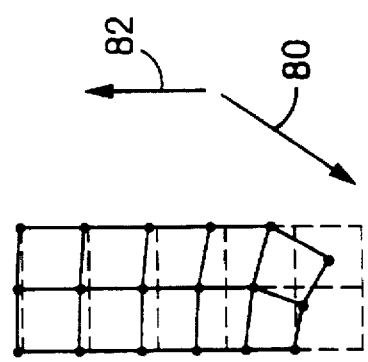

Referring now to FIGS. 3A–3C, material displacements in a film are illustrated. The excitation of the waveguide modes gives rise to material displacements in the film (shown schematically by the spatially varying grid in the figures) which include in 75a–75d and out-of-plane 77a–77c displacements in the film. The lowest four waveguide modes that propagate in a typical unsupported polyimide film at a wavevector-thickness product of 2.5 are illustrated in FIG. 3A. The propagation speeds for each mode are shown in the figure insets. The number, velocity and spatial character of these modes scales with the product of the acoustic wavevector and the film thickness.

Although the waveguide modes generated in the film all propagate along the surface of the film, the motions associated with each mode involve shear and longitudinal strains both in and out of the plane of the film. Referring now to FIGS. 3B and 3C, a diagram of the lowest order waveguide mode in the large wavevector-thickness limit illustrates the in (indicated by the arrow 80) and out-of-plane (indicated by the arrow 82) shear and longitudinal motions associated with this mode.

Figure 4:
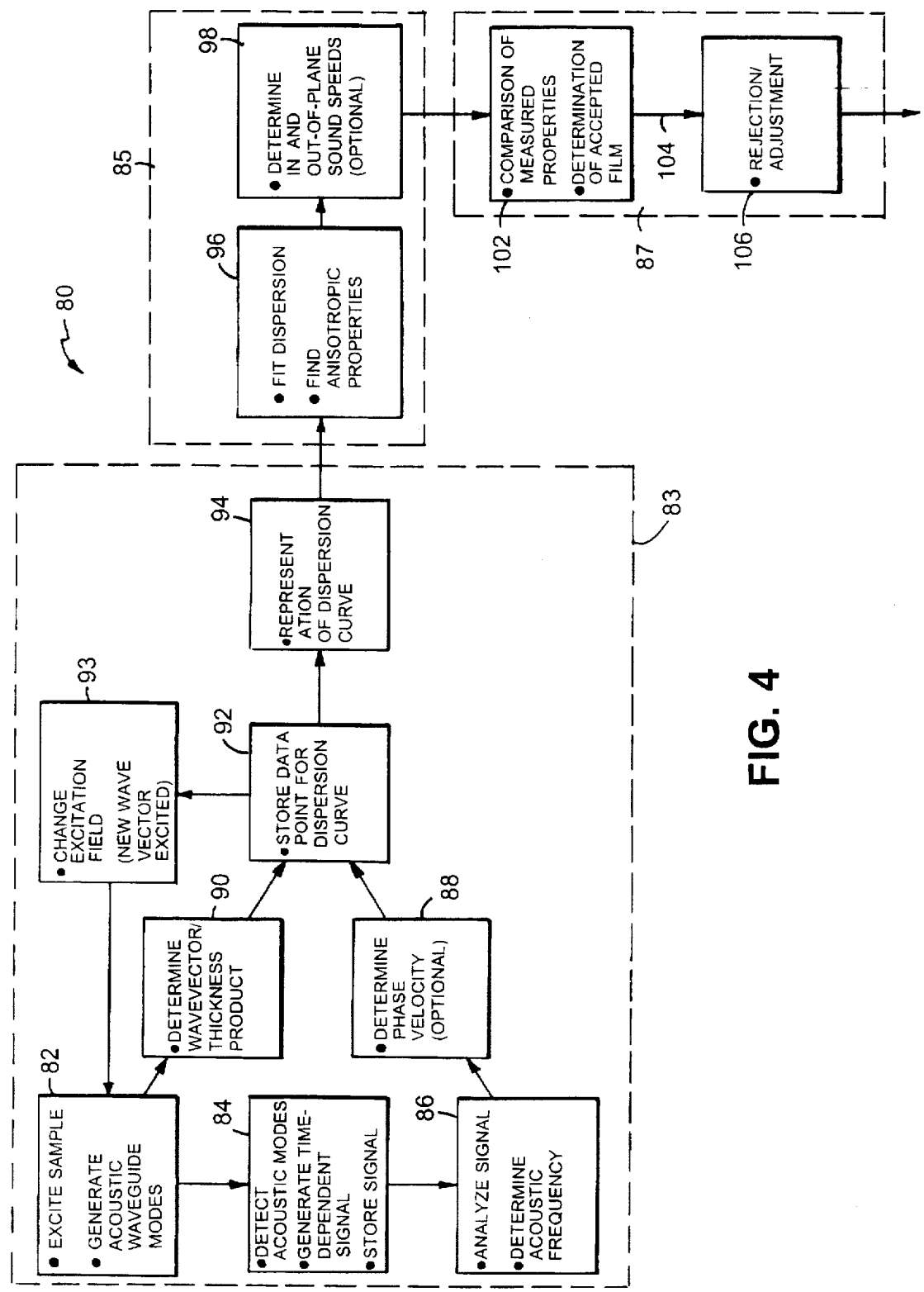
FIG. 4 is a block diagram of the steps used for determining the anisotropic mechanical properties of thin films.

Referring now to FIG. 4, an overview of the process, the method 80 used to determine the anisotropic mechanical properties of a film includes a series of data generation steps 83, described above, used to measure and store the dispersion characteristics of a particular film; a series of data analysis steps 85 for analyzing the resulting data to determine the anisotropic material properties of the film; and, a series of process control steps 87 for accepting or rejecting the film-containing device on the basis of the determined film properties.

The data generation steps 83 begin with an optical excitation step 82, as described above, involving irradiation of the film with the spatially periodic, time-dependent optical field. Once excited in the film, a sampling step 84 using a probe pulse is used to monitor the excited acoustic modes, and the diffracted component of a probe pulse is detected using a high-bandwidth photodetector, thereby producing a light-induced signal having features indicating the dynamical behavior of the waveguide modes. After detection, the signal is measured with a digital-signal analyzer, and stored in a computer as an array of x-y points. As described above, a single laser shot can be detected, or, in order to increase the signal-to-noise ratio of the detected signal, multiple shots can be detected, averaged, and then stored in the computer. Once in a suitable form, the stored time-dependent signal is processed with an analyzing step 86 which involves the use of a numerical algorithm to determine the frequencies of the excited waveguide modes. Most preferably, fast Fourier transform routines (FFT) or linear prediction algorithms known in the art, such as those described in *Numerical Recipes in C* (1994), are used with the computer to process the x-y array of points. The FFT of the time-dependent signal yields a frequency which is then processed 88 to determine the phase velocity of one or more of the excited waveguide modes.

In addition to the phase velocity, the wavevector of the waveguide mode and the film thickness can be used to determine the mode dispersion. The magnitude (q) of the wavevector may be determined 90 by measuring the angle θ between the excitation beams having a wavelength $\lambda_l$ using the equation $q=4\pi\sin(\theta/2)(\lambda_l)^{-1}=2\pi/\Lambda$, where $\Lambda$ is the grating wavelength. The thickness of the film can be determined prior to the wavevector calculation step 90 using techniques known in the art, such as the optical ellipsometry or stylus prolifometry techniques. In addition, as discussed above, the film thickness can be determined using the fitting algorithm.

Once determined, the phase velocity and wavevector-thickness product are stored 92 (in, e.g., a computer memory) as a data point; if more than one waveguide mode is excited by the excitation pulses at a particular wavevector (i.e., multiple frequencies are present in the light-induced signal), a data point is generated for each mode. If more data points are desired, a new spatially varying excitation field is generated 93 and used to excite the film at a different wavevector. The initial steps 82–93 of the data generation processes 83 are repeated, if necessary, until a substantial amount of data points are generated and stored in the computer. Typically, four (if the thickness is known) or five (if the thickness is unknown) data points are used. Once generated, the series of data points are collected and stored 94 as an array of x-y values in the computer memory. This data represents the dispersion curve (i.e., the phase velocity as a function of the wavevector-thickness product) for the waveguide modes excited in the film.

Using the series of data analysis steps 85, the x-y array of data points are fit 96 to determine the anisotropic properties using a numerical function generated from a series of matrix equations describing the acoustic properties of transverse isotropic media as discussed above.

Calibration of the system prior to the measurement process allows the relationship between anisotropy and film quality to be determined, thereby allowing the measured anisotropy to be used during a series of process control steps 87 as a criteria to accept or reject the film-containing device. For example, following the data generation and data analysis series of steps 83, 85, the shear and longitudinal speeds of sound in the film are determined, and may be compared 102 to similar speeds of sound for acceptable and unacceptable films. In this case, if the comparison 102 indicates an unacceptable film, a signal 104 is sent to the process controller, resulting in rejection 106 of the film-containing device from the assembly line. Similarly, such a measurement can be made during fabrication of the film. If analysis during any fabrication step indicates that unacceptable films are being fabricated, the signal 104 is sent to the process controller, resulting in adjustment of the parameters of the fabrication method. This process can be repeated iteratively until films having the desired properties are formed.

The following are examples of an analysis of the anisotropic properties of thin films of polyimide.

Sample Preparation

Six polyimide film/silicon substrate samples were fabricated by spin coating and fully curing Dupont's PI2611 precursor solution (BPDA/PDA) on 10 cm-diameter silicon wafers. The thickness of each film was determined by the spin speed and was measured with a DEKTAK 8000 stylus profilometer after the cure. The films had thicknesses of, respectively, 2.40, 2.97, 6.01, 6.95, 7.74, and 8.50±0.05 microns. After the thicknesses were recorded, each film was loaded into a teflon jig. Two identical holes in the side of the jig contacting the silicon side of the film defined the areas to be etched. A 6:1:1 mixture of $HF:HNO_3:CH_3COOH$ etchant was poured into the wells formed by the holes in the jig, and within 5 minutes the acid mixture removed the silicon in these regions. After the etch, the films were rinsed with deionized water and were allowed to dry for 48 hours in a desiccator.

The films resulting from this procedure consisted of polyimide-coated 10-cm silicon wafers with a pair of 2.5-cm holes in each wafer. For each excitation angle, data were collected in two different regions in each of the two exposed areas where the silicon was etched away.

Optical Measurement

Figure 2:
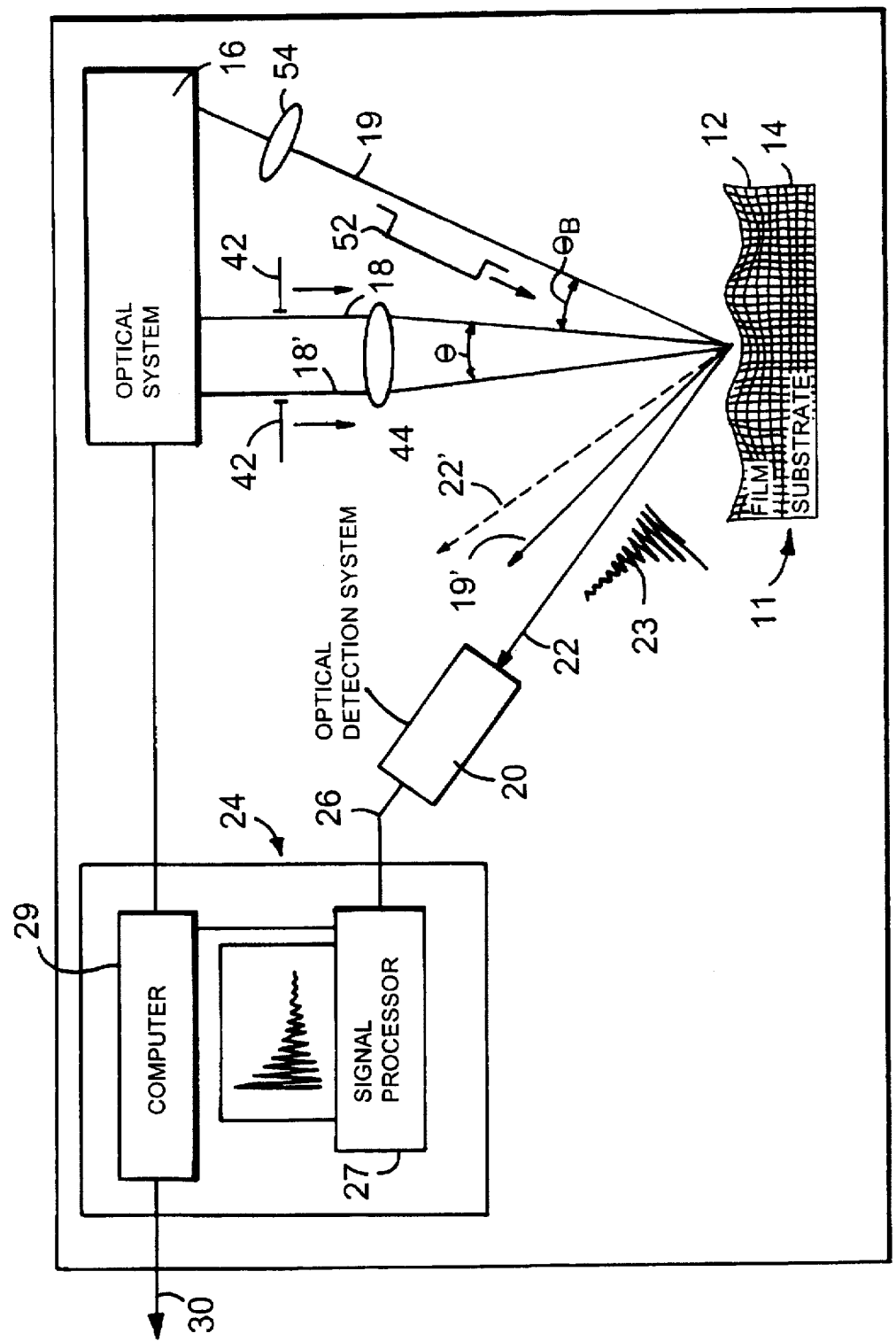
FIG. 2 is a schematic of a film-measurement device used for optically exciting and detecting the anisotropic properties of a thin film.

A detailed description of ISTS optical systems is given in J. A. Rogers et al., J. Appl. Phys. 75:1 (1994) and A. R. Duggal et al., U.S. Ser. No. 07/910,762, the contents of which are incorporated herein by reference. Briefly, referring again to FIGS. 1 and 2, anisotropic material motions in the film are induced by way of the optical excitation system 10 which includes an excitation light source 36 used to generate an optical beam 17. If the carrier frequency of the pulses is below the absorption energy of the film, the optical beam 17 may be passed through one or more non-linear optical devices 38, such as a frequency-doubling or frequency-tripling crystal, which can be used to generate higher-order harmonics (e.g., second or third harmonics) of the fundamental frequency. When the excitation pulse is of suitable frequency, it is passed through a series of beam-splitting optics 40 which allow generation of two excitation beams 18, 18' each containing pulses 42, 42' having durations, e.g., between about 0.1 and 1 ns.

Once generated and separated, the pulses 42, 42' of suitable carrier frequency and time duration are preferably focussed by a lens 44 onto the surface of the film, where they are overlapped in time and space. Optical interference between the overlapped pulses gives rise to a spatially varying intensity pattern, or grating. The acoustic responses consist of counter-propagating waveguide modes, indicated in FIG. 2 by the spatial displacements in the film, which give rise to a time-dependent signal 23 including a damped oscillatory component. The thermal response of the film gives rise to a quasi-steady-state material response which persists until thermal diffusion washes out the temperature grating.

The time-dependent properties of both the waveguide modes and the thermal response are recorded in real-time by monitoring the time-dependent diffraction of the probe beam 19, which is preferably derived from a continuous wave (cw) single-mode laser 46. In order to measure the entire time dependence of the induced anisotropic motions of the film (which, e.g., may take place over several hundreds of microseconds), a well-defined probe waveform 52 is generated by electro-optically modulating the cw probe beam with a modulator 48. Both the duration and shape of the probe waveform 52 are controlled by the modulator 48. Preferably, a square pulse is generated which has a time duration slightly longer than the time-dependent motions in the film.

Once generated and suitably modulated, the probe beam may then be passed through or reflected off of additional optical components 50, such as mirrors, frequency and spatial filters, frequency-doubling crystals, or telescoping lenses, to achieve the desired spatial, energy, and intensity profiles. In order to sample the induced displacements on the surface on the film, the probe pulse 52 is preferably focussed on the film using a lens 54. Alternatively, the excitation 18, 18' and probe 19 beams may be arranged so that a single lens is used to focus all three beams.

The diffracted probe waveform 22 is then detected with a time-resolving photodetector 56 housed in the optical detection mechanism 20. This allows the entire time dependence of the excited region of film to be measured with a single probe waveform. For especially weak signals, a lens 58 may be used to focus the diffracted beam on the optically active region of the detector 56, thereby increasing the intensity of the signal. For particularly noisy or weak signals, signal-enhancing electronics 60, such as high-speed amplifiers, may be used with the optical detection component 20.

In the data reported, waveguide modes in the film were excited using a Q-switched, mode-locked, and cavity-dumped Nd:YAG laser. The output pulse had an energy of 1 millijoule, a wavelength of 1064 nm, a pulse duration of 100 ps, and a repetition rate of up to 1 kHz. The light from this laser was first attenuated and then passed through a lithium triborate (LBO) crystal to yield light at 532 nm, which was then mixed with the remnant 1064 nm radiation in a β-barium borate (BBO) crystal to yield excitation pulses of approximately 20 microjoules at 355 nm. This light was attenuated to yield ~1 microjoule pulses that were used for excitation of the films. During excitation, the 355-nm pulses were passed through a 50% beam splitter and then crossed at the angle Θ. The excitation pulses are focussed using a cylindrical lens to produce a beam size on the film of about 1 cm (z direction) by 300 microns (x direction).

Material motions in the film were recorded in real-time by monitoring the time-dependent diffraction of a probe pulse spatially overlapped with the excitation pulses. The probe pulse was derived from a cw single-mode Argon ion laser (Lexel 3500) producing 1 Watt at 514 nm with a flat intensity profile. This output was electro-optically modulated (Conoptics 380) to yield a square pulse having a temporal width of between 1 and 20 microseconds. The probe beam was focussed to a spot of between 50 and 70 microns in the film. The diffracted component of the probe beam was measured with a fast amplified photodiode (Antel—2 GHz bandwidth). The light-induced signal was then sent to a transient digitizer (Tektronics DSA 602A—1 GHz bandwidth), resulting in generation of digital signal for analysis. The combination of the photodiode and transient digitizer effectively provided a 1 GHz-bandwidth window through which film oscillatory and relaxational motions were monitored.

Data Analysis

Data was then collected at crossing angles which correspond to grating wavelengths Λ of 28.29, 25.30, 23.93, 19.35, 18.21, 16.04, 15.33, 13.75, 12.76, 12.41, 11.04, 10.06, 10.03, 9.05, 8.67, 8.37, 7.49, 7.36, 6.82, 6.67, 6.33, 5.74, 5.67, 5.39, 5.12, 5.11, 4.94, 4.64, 4.56, 4.29, 4.18, and 3.89±0.05 microns. The grating wavelengths were determined with a 3.15-micron unsupported Dupont PI2555 (BTDA/ODA/MPDA) "standard" film whose acoustic response was calibrated using an optical microscope to measure the wavelength of grating patterns burned into a blank silicon wafer.

Figure 5A:
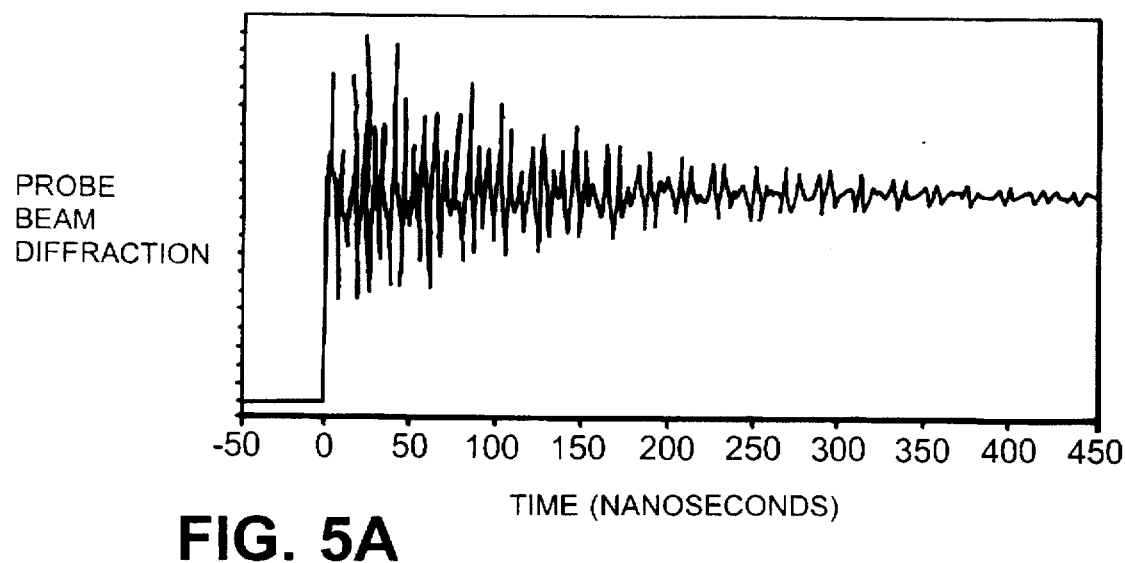
FIGS. 5A and 5B are plots of time-dependent diffracted signals measured using the film measurement device.
Figure 5B:
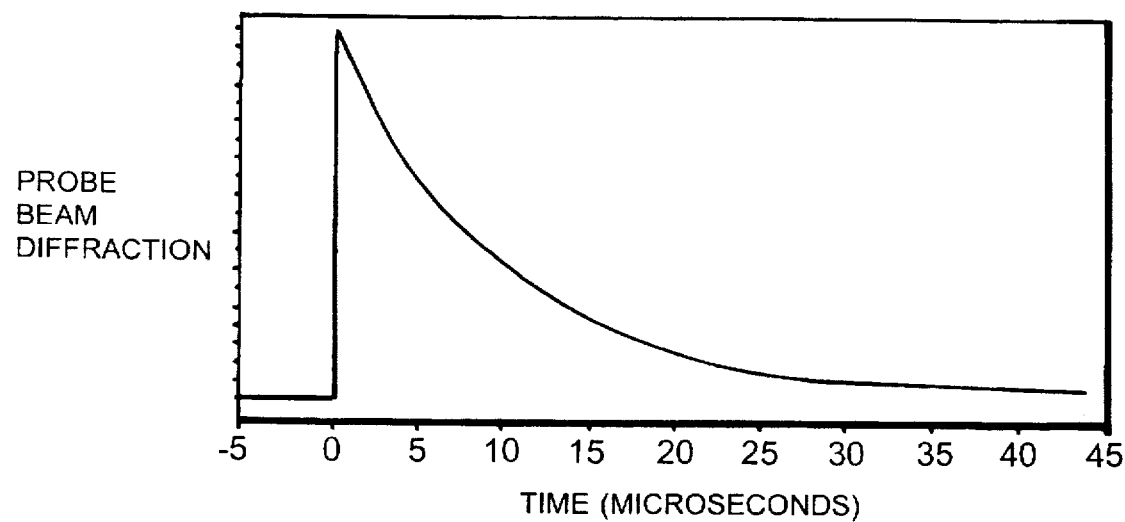

Referring now to FIGS. 5A and 5B, typical data taken from the free-standing polyimide films using the above-identified optical system illustrates the time-dependent nature of the measured signal. The oscillatory component of the data is due to the coherent, periodic motions of the excited waveguide modes. Damping of these modes, shown in the data (after several hundred nanoseconds) as a decrease in the amplitude of subsequent oscillations, is due to viscous losses in the polyimide material. The long-time decay illustrated in FIG. 5B is due to thermal diffusion in and out of the plane of the film; this process washes out the diffraction efficiency of the grating on time scale of a few microseconds.

Figure 6:
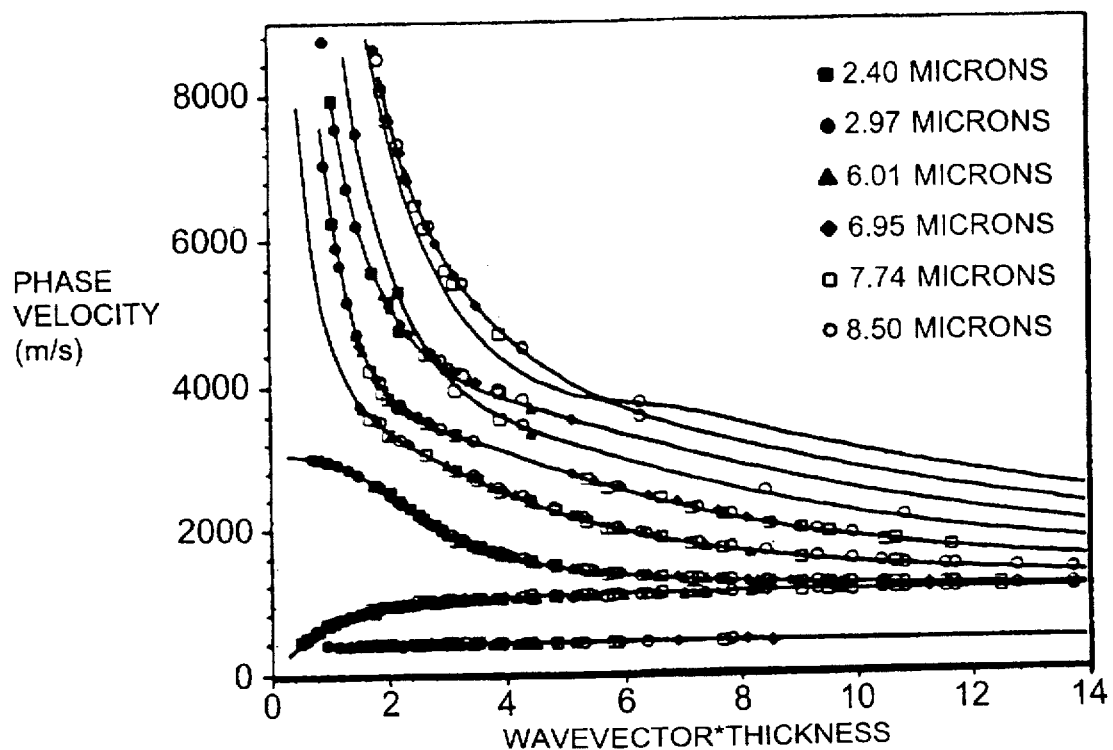
FIG. 6 is a plot of the measured (symbols) and calculated (lines) dispersion of waveguide modes determined according to the invention.

Once collected, the time-dependent data is used to determine the dependence of the phase velocity of the waveguide mode on the wavevector-thickness product. Referring now to FIG. 6, a dispersion diagram can be used to graphically plot this data (represented in the figure by the symbols). The calculated dispersion (lines) of the waveguide mode phase velocities, computed as discussed above, indicates that the model can very accurately describe the measured waveguide dispersion. The model, therefore, can be used to determine the in and out-of-plane shear and longitudinal acoustic speeds of each film. The values of these acoustic velocities (given in table 1, below) are determined using the computer program listed in appendix A, and are consistent with the belief that there is in-plane ordering of the polymer chains in this material.

TABLE 1

Mechanical properties of polyimide films (BPDA/PDA)

| MECHANICAL PROPERTY | BEST FIT VALUE |
| --- | --- |
| In-Plane Longitudinal Acoustic Speed | 3500 ± 20 m/s |
| In-Plane Shear Acoustic Speed | 2000 ± 15 m/s |
| Out-of-Plane Longitudinal Acoustic Speed | 2330 ± 15 m/s |
| Out-of-Plane Shear Acoustic Speed | 1090 ± 7.5 m/s |

The best fit values in Table 1 indicate the accuracy of the measurement to be within 1% of the actual values as measured by a 90% confidence interval F-test.

Other Embodiments

Other embodiments are within the scope of the invention. For example, light sources other than Nd:YAG lasers may be used to optically excite the film. Suitable lasers include, among others, Nd:YLF, ion (e.g., argon and krypton), Ti:Sapphire, diode, $CO_2$, holmium, excimer, dye, and metal-vapor lasers. Typically, these lasers are electro-optically or acousto-optically modulated (using, e.g., mode-locking and Q-switching devices known in the art) to produce suitable energies (i.e., between 0.1 and 5 microjoules/pulse) and pulse durations (i.e., less than about 1 ns). If the fundamental frequency of the light source is lower than the absorption frequency of the film, the light may be passed through a non-linear optical media to generate light at a higher energy. If the wavelengths of the two excitation pulses are such that the pulses are attenuated by the beam-splitting optics, the order of the harmonic generation and beam splitting may be reversed, i.e., two pulses of the fundamental frequency are first generated, and then each pulse is independently passed through a non-linear optical device (or devices) to increase the frequency. In addition, the repetition rate of the pulses must be high enough to allow suitable data averaging, but low enough to allow the thermal properties of the film to recover between laser shots. Preferably, the repetition rate is between 1 and 2000 Hz, with the rate being adjusted for measurement of different types of films. For films which easily damage, it is preferable to reduce the repetition rate of the excitation laser; a reduction in the number of excitation pulses reduces the number of heating cycles which can potentially damage thin, fragile films.

Similarly, light sources other than cw argon ion lasers may be used as the probe laser. Alternative lasers include diode and krypton ion lasers. Alternatively, a pulsed laser producing a pulse duration greater than about 500 ns may be used as the probe laser. Pulsed light sources which may be used to generate the probe beam include Q-switched Nd:YAG, Nd:YLF, Ti:Sapphire, diode, $CO_2$, holmium, excimer, dye, and metal-vapor lasers.

In addition to the anisotropic sound speeds, the method described herein can be used to determine the visco-elastic properties and thermal diffusivities in supported and free-standing isotropic polyimide films. In addition, by adjusting the irradiated region of the film, the method can be used to locate and map out regions of mechanical inhomogeneities in films bound to substrates.

Other embodiments are within the scope of the following claims.

APPENDIX A

```
/*
  fitting function for unsupported anisotropic plate
*/

/*last modified 8/29/93*/

/*matches the isotropic model on 8/29/93*/

/*
  x[0] is the kh value
  x[1] is the mode number
  p[0] is the out-of-plane shear velocity in m/s
  p[1] is the in-plane shear velocity in m/s
  p[2] is the out-of-plane longitudinal velocity in m/s
  p[3] is the in-plane longitudinal velocity in m/s

*/ include "matrix.h"
include "math.h"
#include "stdio.h"
#include "/marla/john/complex/complex.h"

#define N 6
define LARGE 1e40 define SMALL .01
define BIG 100
#define NUMPARAMS 4
#define NEAR 0.001
#define RTRATIO 0.7
#define BISINT 10.0
define VACC 1.0e-6 double genlamvel(y,q)
```

```
vector y;
vector q;

{
  int index, nroots;
  int getvs();
  vector vs, r;
  double retval;
  double alpha, bvect, b;

index=y[1];
  r=vdim(4);
  vs=vdim(index+1);
  if(!vs){
    fprintf(stderr,"no memory in vs\n");
    exit(-1);
  }

/*converting input velocities into scaled moduli
        (i.e. moduli divided by the density*/ r[0]=q[0]*q[0];
  r[1]=q[3]*q[3];
  r[3]=q[2]*q[2];
  r[2]=-2.0*q[1]*q[1]+r[3];

nroots=getvs(y[0],r,vs,BISINT,VACC,index+1);
  vfree(r);

alpha=0.0;
  bvect=0.0;
  b=0.0;

if(nroots!=(index+1)){
    printf("trouble with root finding in the fitting routine\n");
    vfree(vs);
```

```
    return(1000000.0);
  }
  else{
    retval=vs[index];
    vfree(vs);
    return(retval);
  }
} double funceval(x,p)
vector x,p;

{
  int i,j;
  comatrix modematrix, matrcalc();
  double deterval;
  complex tempor, comdeter();

modematrix = matrcalc(x[0],x[1],p[0],p[1],p[2],p[3]);
  tempor = comdeter(modematrix,NUMPARAMS);
  comfree(modematrix, NUMPARAMS, NUMPARAMS);

if(fabs(tempor.im) > fabs(tempor.re))
    deterval = tempor.im;
  else
    deterval = tempor.re;

/* determinant should be either completely imaginary
          or completely real */
  if(fabs(tempor.im)/fabs(tempor.re)>SMALL &&
          fabs(tempor.im)/fabs(tempor.re)<BIG){
    fprintf(stderr, "there are real and imaginary parts to determinant\n");
    fprintf(stderr, "\nreal = %le, imag = %le\n", tempor.re, tempor.im);
    for (i=0; i<2; i++)
      fprintf(stderr, "x[%d] = %le\t",i, x[i]);
/*
    for (i=0; i<6; i++)
```

3

```
        fprintf(stderr, "p[%d] = %le\t",i, p[i]);
*/
  }
   return (deterval);
}
/*returns the matrix whose determinant is to be set to zero*/ comatrix matrcalc(v,kh,c44,c33,c23,c22)
double v, kh;
double c44, c33, c23, c22;
{ comatrix b;
  covector alpha;
  covector bvect;
  covector exppb, expmb;
  covector evalalpha2(), evalb();
  int i;

b=comdim(4,4);
  exppb=covdim(4);
  expmb=covdim(4);
  if(!expmb){
    fprintf(stderr,"no memory\n");
    exit(-1);
  } bvect=evalb(c44,c33,c23,c22,v);
  alpha=evalalpha2(bvect,c44,c33,c23,v);

for(i=0;i<4;i++){
    exppb[i]=Cexp(Cmul(Complex(0.0,kh/2.0),bvect[i]));
    expmb[i]=Cexp(Cmul(Complex(0.0,-1.0*kh),bvect[i]));
  } for(i=0;i<4;i++){
    b[0][i]=Cadd(RCmul(c23,alpha[i]),RCmul(c33,bvect[i]));
    b[0][i]=Cmul(b[0][i],exppb[i]);
```

```
  } for(i=0;i<4;i++){
   b[1][i]=Cmul(b[0][i],expmb[i]);
  } for(i=0;i<4;i++){
   b[2][i]=Cadd(Cmul(bvect[i],alpha[i]),Complex(1.0,0.0));
   b[2][i]=Cmul(b[2][i],RCmul(c44,exppb[i]));
  } for(i=0;i<4;i++){
   b[3][i]=Cmul(b[2][i],expmb[i]);
  } covfree(bvect);
  covfree(exppb);
  covfree(expmb);
  covfree(alpha);

return (b);

} covector evalb(c44,c33,c23,c22,v)
double c44, c33, c23, c22, v;
{ int i;
  double a, b, c;
  covector retval;
  complex b1sqrd, b2sqrd;

retval=covdim(4);
  if(!retval){
    fprintf(stderr,"no memory in evalb\n");
    exit(-1);
  }
```

```
    a=-1.0*c44*c33;

b=(c23+c44)*(c23+c44)+v*v*c44-c44*c44+v*v*c33-c22*c33;

c=-1.0*(c22-v*v)*(c44-v*v);

b1sqrd=Cadd(Complex(-b,0.0),Csqrt(Complex(b*b-4.0*a*c,0.0)));

b1sqrd=Cdiv(b1sqrd,Complex(2.0*a,0.0));

b2sqrd=Csub(Complex(-b,0.0),Csqrt(Complex(b*b-4.0*a*c,0.0)));

b2sqrd=Cdiv(b2sqrd,Complex(2.0*a,0.0));

retval[0]=Csqrt(b1sqrd);
    retval[1]=Cmul(Complex(-1.0,0),retval[0]);
    retval[2]=Csqrt(b2sqrd);
    retval[3]=Cmul(Complex(-1.0,0.0),retval[2]);

return(retval);

} covector evalalpha2(b,c44,c33,c23,v)
covector b;
double c44, c33, c23, v;
{
  int i;
  covector retval;
  complex tempnum, tempdenom;

retval=covdim(4);
  if(!retval){
    fprintf(stderr,"no memory in evalalpha\n");
    exit(-1);
  } for(i=0;i<4;i++){
    tempnum=Csub(Complex(v*v-c44,0.0),RCmul(c33,Cmul(b[i],b[i])));
    tempdenom=RCmul(c23+c44,b[i]);
```

```
    retval[i]=Cdiv(tempnum,tempdenom);
  } return (retval);

}

/*
    finds the velocity values that solve determinant eq. consistent with kh
    and p values. Uses interval bisint to step through the possible velocity
    values using bisection routine. bisint must be smaller than closest velocity
    spacing. vacc is accuracy for bisection routine. At finish, vs will contain
    velocity values and the number of values will be returned.
*/ getvs(kh, params, vels, bisint, vacc, maxroots)
double kh, bisint, vacc;
vector params, vels;
int maxroots;
{
  double c2, c1, lastroot=0.0, root, frtbis(), maxv;
  double vtr, vlg;
  int nroots=0, done=0;

vtr=sqrt(params[0]);
  vlg=sqrt(params[3]);

maxv=10000.0;
  c1=100.1;

c2 = c1 + bisint;
  while(!done){
    /* watch out for solution near vlg */
    if((vlg<c2+NEAR) && (vlg>c1-NEAR)){
      if( ((root=frtbis(kh,params,c1,vlg-NEAR,vacc))>SMALL)
            && fabs(root-lastroot)>vacc ){
        fprintf(stderr, "got root %le in vlg loop\n", root);
        vels[nroots] = root;
/*      printf("got a root and the value is %le\n",root);*/
        lastroot = root;
```

```
        nroots++;
        if(nroots == maxroots)
          done = 1;
      }
      c1 = vlg + NEAR;
      c2 += NEAR;
    }
    /* watch out for solution near vtr */
    if((vtr<c2+NEAR) && (vtr>c1-NEAR)){
      if( (((root=frtbis(kh,params,c1,vtr-NEAR,vacc))>SMALL)
              && fabs(root-lastroot)>vacc) && !done){
        fprintf(stderr, "got root %le in vtr loop\n", root);
        vels[nroots] = root;
/*      printf("got a root and the value is %le\n",root);*/
        lastroot = root;
        nroots++;
        if(nroots == maxroots)
          done = 1;
      }
      c1 = vtr + NEAR;
      c2 += NEAR;
    } if( (((root=frtbis(kh,params,c1,c2,vacc))>SMALL)
            && fabs(root-lastroot)>vacc) && !done ){
      vels[nroots] = root;
/*    printf("got a root and the value is %le\n",root);*/
      lastroot = root;
      nroots++;
      if(nroots == maxroots)
        done = 1;
    } c1 = c2;
    c2 += bisint;
    if (c2 > maxv)
      done = 1;
  }
  return nroots;
}
```

```
/* keeps all roots */ getallvs(kh, params, vels, bisint, vacc, maxroots)
double kh, bisint, vacc;
vector params, vels;
int maxroots;
{
  double c2, c1, lastroot=0.0, root, frtbis(), maxv;
  int nroots=0, done=0;

maxv=10000.0;
  c1=0.1;

c2 = c1 + bisint;
  while(!done){
    if( ((root=frtbis(kh,params,c1,c2,vacc))>SMALL)
           && fabs(root-lastroot)>vacc ){
      vels[nroots] = root;
      lastroot = root;
      nroots++;
      if(nroots == maxroots)
        done = 1;
    } c1 = c2;
    c2 += bisint;
    if (c2 > maxv)
      done = 1;
  }
  return nroots;
}
```

```
define JMAX 40 double frtbis(kh,pa,v1,v2,vacc)
```

9

```
double kh, v1,v2,vacc;
vector pa;

{
    int j;
    double dv, f, fmid, vmid, rtb, z[2], funceval();

if(!z){
      fprintf(stderr,"no memory in frtbis\n");
      exit(-1);
    } z[1] = kh;

z[0] = v1;
    f=funceval(z,pa);

z[0] = v2;
    fmid=funceval(z,pa);

if (f*fmid >= 0.0) return (0.0);

rtb = f < 0.0 ? (dv=v2-v1,v1) : (dv=v1-v2,v2);
    for (j=1;j<=JMAX;j++) {
            vmid = rtb+(dv *= 0.5);
            z[0] = vmid;
            fmid=funceval(z,pa);
            if (fmid==NULL){
              vfree(z);
              return(0.0);}
            if (fmid <= 0.0) rtb=vmid;
            if (fabs(dv) < vacc || fmid == 0.0){
              vfree(z);
              return rtb;}
    }
    fprintf(stderr, "Too many bisections in FRTBIS\n");
    vfree(z);
    return (0.0);
}
```

10

```
#undef JMAX

/* -h<y<0 is film, y>0 is substrate */ getdispl(potents, vs, y, clgf, ctrf, k, uy, uz, numvs)
comatrix potents;
vector vs;
covector uy, uz;
double clgf, ctrf, k,y;
{
  int i;
  complex ik;
  covector a, b, c, d;
  covector o, p;

a = covdim(numvs);
  b = covdim(numvs);
  c = covdim(numvs);
  d = covdim(numvs);
  o = covdim(numvs);
  p = covdim(numvs);
  if(!p){
    fprintf(stderr,"no memory\n");
    exit(-1);
  } ik = Complex(0.0,k);
  if (y<0.0){
    for(i=0; i<numvs; i++){
      o[i] = Csqrt(Complex(1 - vs[i]*vs[i]/(clgf*clgf),0));
      p[i] = Csqrt(Complex(1 - vs[i]*vs[i]/(ctrf*ctrf),0));
      a[i] = Cmul(potents[i][0],Cexp(RCmul(k*y,o[i])));
      b[i] = Cmul(potents[i][1],Cexp(RCmul(-k*y,o[i])));
      c[i] = Cmul(potents[i][2],Cexp(RCmul(k*y,p[i])));
      d[i] = Cmul(potents[i][3],Cexp(RCmul(-k*y,p[i])));
    }
  }
  else{
```

```
    for(i=0; i<numvs; i++){
      o[i] = Csqrt(Complex(1 - vs[i]*vs[i]/(clgf*clgf),0));
      p[i] = Csqrt(Complex(1 - vs[i]*vs[i]/(ctrf*ctrf),0));
      a[i].re = 0.0;
      a[i].im = 0.0;
      b[i] = Cmul(potents[i][4],Cexp(RCmul(-k*y,o[i])));
      c[i].re = 0.0;
      c[i].im = 0.0;
      d[i] = Cmul(potents[i][5],Cexp(RCmul(-k*y,p[i])));
     }
  } for(i=0; i<numvs; i++){
    uy[i] = Cadd(Cmul(RCmul(k,o[i]),Csub(a[i],b[i]))
                ,Cmul(ik,Cadd(c[i],d[i])));
    uz[i] = Cadd(Cmul(RCmul(k,p[i]),Csub(d[i],c[i]))
                ,Cmul(ik,Cadd(a[i],b[i])));
  }
  cvfree(a);
  cvfree(b);
  cvfree(c);
  cvfree(d);
  cvfree(o);
  cvfree(p);

} getlgtrdispl(potents, vs, y, clgf, ctrf, k, uyl, uzl, uyt, uzt, numvs)
comatrix potents;
vector vs;
covector uyl, uzl, uyt, uzt;
double clgf, ctrf, k,y;
{
  int i;
  complex ik;
  covector a, b, c, d;
  covector o, p;

a = covdim(numvs);
```

12

```
b = covdim(numvs);
c = covdim(numvs);
d = covdim(numvs);
o = covdim(numvs);
p = covdim(numvs);
if(!p){
  fprintf(stderr,"no memory\n");
  exit(-1);
} ik = Complex(0.0,k);
if (y>0.0){
  for(i=0; i<numvs; i++){
    o[i] = Csqrt(Complex(1 - vs[i]*vs[i]/(clgf*clgf),0));
    p[i] = Csqrt(Complex(1 - vs[i]*vs[i]/(ctrf*ctrf),0));
    a[i] = Cmul(potents[i][0],Cexp(RCmul(-k*y,o[i])));
    b[i] = Cmul(potents[i][1],Cexp(RCmul(k*y,o[i])));
    c[i] = Cmul(potents[i][2],Cexp(RCmul(-k*y,p[i])));
    d[i] = Cmul(potents[i][3],Cexp(RCmul(k*y,p[i])));
  }
}
else{
  for(i=0; i<numvs; i++){
    o[i] = Csqrt(Complex(1 - vs[i]*vs[i]/(clgf*clgf),0));
    p[i] = Csqrt(Complex(1 - vs[i]*vs[i]/(ctrf*ctrf),0));
    a[i].re = 0.0;
    a[i].im = 0.0;
    b[i] = Cmul(potents[i][4],Cexp(RCmul(k*y,o[i])));
    c[i].re = 0.0;
    c[i].im = 0.0;
    d[i] = Cmul(potents[i][5],Cexp(RCmul(k*y,p[i])));
  }
} for(i=0; i<numvs; i++){
  uyl[i] = Cmul(RCmul(k,o[i]),Csub(a[i],b[i]));
  uzl[i] = Cmul(ik,Cadd(a[i],b[i]));
  uyt[i] = Cmul(ik,Cadd(c[i],d[i]));
  uzt[i] = Cmul(RCmul(k,p[i]),Csub(d[i],c[i]));
}
```

```
    cvfree(a);
    cvfree(b);
    cvfree(c);
    cvfree(d);
    cvfree(o);
    cvfree(p);

}
```

APPENDIX B

```
/*
  fitting function for supported anisotropic plate
*/

/*
  x[0] is the kh value
  x[1] is the mode number
  p[0] is the out-of-plane shear velocity in m/s
  p[1] is the in-plane shear velocity in m/s
  p[2] is the out-of-plane longitudinal velocity in m/s
  p[3] is the in-plane longitudinal velocity in m/s

*/ include "matrix.h"
include "math.h"
#include "stdio.h"
#include "complex.h"

#define N 6
define LARGE 1e40 define SMALL .01
define BIG 100.0
#define NUMPARAMS 10
#define NEAR 0.001
#define RTRATIO 0.7
#define BISINT 50.0
define VACC 1e-6 double genlamvel(y,q)
vector y;
vector q;

{
```

```
   int index, nroots;
   int getvs();
   vector vs, r, h, d;
   double retval;
   double alpha, bvect, b;

index=y[1];
r=vdim(10);
h=vdim(2);
d=vdim(3);
vs=vdim(index+1);
if(!vs){
   fprintf(stderr,"no memory in vs\n");
   exit(-1);
}
```

/*converting input velocities into scaled moduli (i.e. moduli divided by the density*/

```
r[0]=q[0]*q[0]*q[4];
r[1]=q[3]*q[3]*q[4];
r[3]=q[2]*q[2]*q[4];
r[2]=-2.0*q[1]*q[1]*q[4]+r[3];

r[4]=q[0]*q[0]*q[4];
r[5]=q[3]*q[3]*q[4];
r[7]=q[2]*q[2]*q[4];
r[6]=-2.0*q[1]*q[1]*q[4]+r[3];

r[8]=q[5]*q[5]*q[7];
r[9]=q[6]*q[6]*q[7];

h[0]=0.5;
h[1]=1.0;

d[0]=q[4];
d[1]=q[4];
```

```
    d[2]=q[7];

nroots=getvs(y[0],h,r,d,vs,BISINT,VACC,index+1);
   vfree(r);

alpha=0.0;
  bvect=0.0;
  b=0.0;

if(nroots!=(index+1)){
    printf("trouble with root finding in the fitting routine\n");
    vfree(vs);
    return(1000000.0);
  }
  else{
   retval=vs[index];
   vfree(vs);
   return(retval);
  }
} double funceval(x,h,p,r)
vector x,h,p,r;

{
  int i,j;
  comatrix modematrix, matrcalc();
  double deterval;
  complex tempor, comdeter();

modematrix = matrcalc(x[0],x[1],h[0],h[1],p[0],p[1],p[2],p[3],p[4],
     p[5],p[6],p[7],p[8],p[9],r[0],r[1],r[2]);
  tempor = comdeter(modematrix,NUMPARAMS);
  comfree(modematrix, NUMPARAMS, NUMPARAMS);

/* printf("\n bc det is %le and %le",tempor.re, tempor.im);*/
```

```
    if(fabs(tempor.im) > fabs(tempor.re))
       deterval = tempor.im;
    else
       deterval = tempor.re;

/* determinant should be either completely imaginary or completely real
     */
    if(fabs(tempor.im)/fabs(tempor.re)>SMALL &&
              fabs(tempor.im)/fabs(tempor.re)<BIG){
       fprintf(stderr, "there are real and imaginary parts to determinant\n");
       fprintf(stderr, "\nreal = %le, imag = %le\n", tempor.re, tempor.im);
       for (i=0; i<2; i++)
          fprintf(stderr, "x[%d] = %le\t",i, x[i]);
    /*
       for (i=0; i<6; i++)
          fprintf(stderr, "p[%d] = %le\t",i, p[i]);
     */
    } return (deterval);
}
/*returns the matrix whose determinant is to be set to zero*/ comatrix matrcalc(v,k,h1,h2,ca44,ca33,ca23,ca22,cb44,cb33,cb23,cb22,
              sc44,sc33,r1,r2,sr)
double v, k, h1, h2, r1, r2;
double ca44, ca33, ca23, ca22, cb44, cb33, cb23, cb22;
double sc44,sc33,sr;
{ comatrix b;
   covector alpha1;
   covector b1vect;
   covector alpha2;
   covector b2vect;
   covector sb1vect;
   covector salpha1;
   covector exp1b1, exp2b1;
   covector exp2b2, exp1b2;
   covector evalalpha2(), evalb(), sevalb(), sevalalpha2();
```

4

```
    complex temp, comdeter();
    double sc23;
    int i,j;

b=comdim(10,10);
    exp1b1=covdim(4);
    exp2b1=covdim(4);
    exp1b2=covdim(4);
    exp2b2=covdim(4);
/* if(!expmb){
      fprintf(stderr,"no memory\n");
      exit(-1);
    }*/ b1vect=evalb(ca44,ca33,ca23,ca22,r1,v);
    alpha1=evalalpha2(b1vect,ca44,ca33,ca23,r1,v);
    b2vect=evalb(cb44,cb33,cb23,cb22,r2,v);
    alpha2=evalalpha2(b2vect,cb44,cb33,cb23,r2,v);
    sb1vect=sevalb(sc44,sc33,sr,v);
    salpha1=sevalalpha2(sc44,sc33,sr,v,sb1vect);

for(i=0;i<4;i++){
     exp1b1[i]=Cexp(Cmul(Complex(0.0,k*h1),b1vect[i]));
     exp2b1[i]=Cexp(Cmul(Complex(0.0,k*h1),b2vect[i]));
    } for(i=0;i<4;i++){
     exp1b2[i]=Cexp(Cmul(Complex(0.0,k*h2),b1vect[i]));
     exp2b2[i]=Cexp(Cmul(Complex(0.0,k*h2),b2vect[i]));
    }
    sc23 = sc33 - 2.0*sc44;

/*Vanishing of vertical compressional stress at bottom surface (x3=0)*/ for(i=0;i<4;i++){
     b[0][i]=Cadd(RCmul(ca23,alpha1[i]),RCmul(ca33,b1vect[i]));

}
     for(j=4;j<8;j++){
     b[0][j]=Complex(0.0,0.0);
```

```
         }
       for(j=8;j<10;j++) {
         i=j-8;
         temp=Cadd(RCmul(sc23,salpha1[i]),RCmul(sc33,sb1vect[i]));
         b[0][j]=RCmul(-1.0,temp);
       }

/*Vanishing of vertical compressional stress at top surface (x3=h2)*/
                  6x6   Determinant
       for(j=4;j<8;j++){
         i=j-4;
         temp=Cadd(RCmul(cb23,alpha2[i]),RCmul(cb33,b2vect[i]));
         b[1][j]=Cmul(temp,exp2b2[i]);
       }
         for(j=0;j<4;j++){
         b[1][j]=Complex(0.0,0.0);
         } for(j=8;j<10;j++){
         b[1][j]=Complex(0.0,0.0);
       }

/*Vanishing of sagittal shear stress at bottom surface (x3=0)*/ for(i=0;i<4;i++){ temp=Cadd(Cmul(b1vect[i],alpha1[i]),Complex(1.0,0.0));
         b[2][i]=Cmul(temp,Complex(ca44,0.0));
       } for(j=4;j<8;j++){
         b[2][j] = Complex(0.0,0.0);
       } for(i=8;i<10;i++) {
         j=i-8;
         temp=Cadd(Cmul(sb1vect[j],salpha1[j]),Complex(1.0,0.0));
```

6

```
      temp=Cmul(temp,Complex(sc44,0.0));
      b[2][i]=RCmul(-1.0,temp);
    }

/*Vanishing of sagittal shear stress at top surface (x3=h2)*/ for(j=4;j<8;j++){
      i=j-4;

temp=Cadd(Cmul(b2vect[i],alpha2[i]),Complex(1.0,0.0));
      temp=RCmul(cb44,temp);
   /* temp=Cdiv(b[5][j],exp2b1[i]);*/
      b[3][j]=Cmul(temp,exp2b2[i]);
     }
      for(j=0;j<4;j++){
      b[3][j]=Complex(0.0,0.0);
    }
     for(j=8;j<10;j++){
      b[3][j]=Complex(0.0,0.0);
    }

/*Continuity of vertical compressional stress at x3=h1*/ for(i=0;i<4;i++){
     temp=Cadd(RCmul(ca23,alpha1[i]),RCmul(ca33,b1vect[i]));
     b[4][i]=Cmul(temp,exp1b1[i]);
    }
     for(j=4;j<8;j++){
      i=j-4;
     temp=Cadd(RCmul(cb23,alpha2[i]),RCmul(cb33,b2vect[i]));
     temp=Cmul(temp,exp2b1[i]);
     b[4][j]=RCmul(-1.0,temp);
    } for(j=8;j<10;j++){
     b[4][j]=Complex(0.0,0.0);
    }

/*Continuity of sagittal shear stress at x3=h1*/
```

```
for(i=0;i<4;i++){
 temp=Cadd(Cmul(b1vect[i],alpha1[i]),Complex(1.0,0.0));
 temp=RCmul(ca44,temp);
 b[5][i]=Cmul(temp,exp1b1[i]);
}
 for(j=4;j<8;j++){
 i=j-4;
 temp=Cadd(Cmul(b2vect[i],alpha2[i]),Complex(1.0,0.0));
 temp=RCmul(cb44,temp);
 temp=Cmul(temp,exp2b1[i]);
 b[5][j]=RCmul(-1.0,temp);
 } for(j=8;j<10;j++){
 b[5][j]=Complex(0.0,0.0);
}
```

/*Continuity of vertical particle displacement at x3=h1*/

```
for(i=0;i<4;i++){
 b[6][i]=exp1b1[i];
}
for(j=4;j<8;j++){
 i=j-4;
 b[6][j]=RCmul(-1.0,exp2b1[i]);
} for(j=8;j<10;j++){
 b[6][j]=Complex(0.0,0.0);
}
```

/*Continuity of longitudinal particle displacement at x3=h1*/

```
for(i=0;i<4;i++){
 b[7][i]=Cmul(alpha1[i],exp1b1[i]);
}
for(j=4;j<8;j++){
```

8

```
   i=j-4;
   b[7][j]=RCmul(-1.0,Cmul(alpha2[i],exp2b1[i]));
 } for(j=8;j<10;j++){
   b[7][j]=Complex(0.0,0.0);
 }

/*Continuity of vertical particle displacement at substrate interface */ for(i=0;i<4;i++) b[8][i]=Complex(1.0,0.0);

for(i=4;i<8;i++) b[8][i]=Complex(0.0,0.0);

for(i=8;i<10;i++) b[8][i]=Complex(-1.0,0.0);

/*Continuity of longitudinal particle displacement at substrate interface*/ for(i=0;i<4;i++) b[9][i]=alpha1[i];

for(i=4;i<8;i++) b[9][i]=Complex(0.0,0.0);

for(i=8;i<10;i++){
   j=i-8;
   b[9][i]=RCmul(-1.0,salpha1[j]);
 }

/*  for(i=0;i<8;i++){
    for(j=0;j<8;j++){
      printf("\nb[%d][%d] is %le and %le",i,j,b[i][j].re,b[i][j].im);
    }}
*/
```

```
    covfree(b1vect);
    covfree(b2vect);
    covfree(exp1b1);
    covfree(exp1b2);
    covfree(exp2b2);
    covfree(exp2b1);
    covfree(alpha1);
    covfree(alpha2);
    covfree(sb1vect);
    covfree(salpha1);

return (b);

} covector evalb(cc44,cc33,cc23,cc22,r,v)
double cc44, cc33, cc23, cc22, r, v;
{ int i;
  double a, b, c, c44, c33, c23, c22;
  covector retval;
  complex b1sqrd, b2sqrd;

retval=covdim(4);
  if(!retval){
    fprintf(stderr,"no memory in evalb\n");
    exit(-1);
  } c44=cc44/r;
  c33=cc33/r;
  c23=cc23/r;
  c22=cc22/r;

a=-1.0*c44*c33;

b=(c23+c44)*(c23+c44)+v*v*c44-c44*c44+v*v*c33-c22*c33;
```

```
        c=-1.0*(c22-v*v)*(c44-v*v);

b1sqrd=Cadd(Complex(-b,0.0),Csqrt(Complex(b*b-4.0*a*c,0.0)));

b1sqrd=Cdiv(b1sqrd,Complex(2.0*a,0.0));

b2sqrd=Csub(Complex(-b,0.0),Csqrt(Complex(b*b-4.0*a*c,0.0)));

b2sqrd=Cdiv(b2sqrd,Complex(2.0*a,0.0));

retval[0]=Csqrt(b1sqrd);
      retval[1]=Cmul(Complex(-1.0,0),retval[0]);
      retval[2]=Csqrt(b2sqrd);
      retval[3]=Cmul(Complex(-1.0,0.0),retval[2]);

return(retval);

} covector evalalpha2(b,cc44,cc33,cc23,r,v)
covector b;
double cc44, cc33, cc23, v,r;
{
  int i;
  covector retval;
  complex tempnum, tempdenom;
  double c44,c33,c23;
  retval=covdim(4);
  if(!retval){
    fprintf(stderr,"no memory in evalalpha\n");
    exit(-1);
  } c44=cc44/r;
  c33=cc33/r;
  c23=cc23/r;

for(i=0;i<4;i++){
    tempnum=Csub(Complex(v*v-c44,0.0),RCmul(c33,Cmul(b[i],b[i])));
```

```
    tempdenom=RCmul(c23+c44,b[i]);
    retval[i]=Cdiv(tempnum,tempdenom);
  } return (retval);

} covector sevalb(cc44,cc33,r,v)
double cc44, cc33, r, v;
{ int i;
  double a, b, c, c44, c33, c23, c22;
  covector retval;
  complex b1sqrd, b2sqrd, temp1, temp2;

retval=covdim(2);
  if(!retval){
    fprintf(stderr,"no memory in evalb\n");
    exit(-1);
  } c44=cc44/r;
  c33=cc33/r;
  c22=c33;
  c23=-2.0*c44 + c33;

a=-1.0*c44*c33;

b=(c23+c44)*(c23+c44)+v*v*c44-c44*c44+v*v*c33-c22*c33;

c=-1.0*(c22-v*v)*(c44-v*v);

b1sqrd=Cadd(Complex(-b,0.0),Csqrt(Complex(b*b-4.0*a*c,0.0)));

b1sqrd=Cdiv(b1sqrd,Complex(2.0*a,0.0));

b2sqrd=Csub(Complex(-b,0.0),Csqrt(Complex(b*b-4.0*a*c,0.0)));
```

```
    b2sqrd=Cdiv(b2sqrd,Complex(2.0*a,0.0));

temp1 = Csqrt(b1sqrd);
  temp2 = Csqrt(b2sqrd);

/* retval[0]=temp1;*/
  retval[0]=RCmul(-1.0,temp1);
/* retval[2]=temp2;*/
  retval[1]=RCmul(-1.0,temp2);

return(retval);

} covector sevalalpha2(cc44,cc33,r,v,b)
covector b;
double cc44, cc33, r,v;
{
  int i;
  covector retval;

complex tempnum, tempdenom, temp;
  double c44,c33,c23;
  retval=covdim(2);

if(!retval){
    fprintf(stderr,"no memory in evalalpha\n");
    exit(-1);
  } c44=cc44/r;
  c33=cc33/r;
  c23=-2.0*c44+c33;

for(i=0;i<2;i++){
    tempnum=Csub(Complex(v*v-c44,0.0),RCmul(c33,Cmul(b[i],b[i])));
    tempdenom=RCmul(c23+c44,b[i]);
```

```
    temp = Cdiv(tempnum,tempdenom);
    retval[i] = temp;
  } return (retval);

}

/*
   finds the velocity values that solve determinant eq. consistent with kh
   and p values. Uses interval bisint to step through the possible velocity
   values using bisection routine. bisint must be smaller than closest
   velocity spacing. vacc is accuracy for bisection routine. At finish, vs
   will contain velocity values and the number of values will be returned.
*/ getvs(k, h, params, r, vels, bisint, vacc, maxroots)
double k, bisint, vacc;
vector h, params, vels, r;
int maxroots;
{
  double c2, c1, lastroot=0.0, root, frtbis(), maxv;
  double vtr1, vlg1, vtr2, vlg2;
  int nroots=0, done=0;

vtr1=sqrt(params[0]/r[0]);
  vlg1=sqrt(params[3]/r[0]);
  vtr2=sqrt(params[4]/r[1]);
  vlg2=sqrt(params[7]/r[1]);

maxv=5341.0;
  c1=100.1;

c2 = c1 + bisint;
  while(!done){
    /* watch out for solution near vlg1 */
```

```
        if((vlg1<c2+NEAR) && (vlg1>c1-NEAR)){
          if( ((root=frtbis(k,h,params,r,c1,vlg1-NEAR,vacc))>SMALL)
                    && fabs(root-lastroot)>vacc ){
            fprintf(stderr, "got root %le in vlg1 loop\n", root);
            vels[nroots] = root;
/*          printf("got a root and the value is %le\n",root);*/
            lastroot = root;
            nroots++;
            if(nroots == maxroots)
              done = 1;
          }
          c1 = vlg1 + NEAR;
          c2 += NEAR;
        }
        /* watch out for solution near vtr1 */
        if((vtr1<c2+NEAR) && (vtr1>c1-NEAR)){
          if( (((root=frtbis(k,h,params,r,c1,vtr1-NEAR,vacc))>SMALL)
                  && fabs(root-lastroot)>vacc) && !done){
            fprintf(stderr, "got root %le in vtr1 loop\n", root);
            vels[nroots] = root;
/*          printf("got a root and the value is %le\n",root);*/
            lastroot = root;
            nroots++;
            if(nroots == maxroots)
              done = 1;
          }
          c1 = vtr1 + NEAR;
          c2 += NEAR;
        }

/* watch out for solution near vlg2 */ if((vlg2<c2+NEAR) && (vlg2>c1-NEAR)){
          if( ((root=frtbis(k,h,params,r,c1,vlg2-NEAR,vacc))>SMALL)
                    && fabs(root-lastroot)>vacc ){
            fprintf(stderr, "got root %le in vlg2 loop\n", root);
            vels[nroots] = root;
/*          printf("got a root and the value is %le\n",root);*/
            lastroot = root;
            nroots++;
```

```
        if(nroots == maxroots)
          done = 1;
      }
      c1 = vlg2 + NEAR;
      c2 += NEAR;
    }
    /* watch out for solution near vtr2 */
    if((vtr2<c2+NEAR) && (vtr2>c1-NEAR)){
      if( (((root=frtbis(k,h,params,r,c1,vtr2-NEAR,vacc))>SMALL)
            && fabs(root-lastroot)>vacc) && !done){
        fprintf(stderr, "got root %le in vtr2 loop\n", root);
        vels[nroots] = root;
/*      printf("got a root and the value is %le\n",root);*/
        lastroot = root;
        nroots++;
        if(nroots == maxroots)
          done = 1;
      }
      c1 = vtr2 + NEAR;
      c2 += NEAR;
    } if( (((root=frtbis(k,h,params,r,c1,c2,vacc))>SMALL)
          && fabs(root-lastroot)>vacc) && !done ){
      vels[nroots] = root;
/*    printf("got a root and the value is %le\n",root);*/
      lastroot = root;
      nroots++;
      if(nroots == maxroots)
        done = 1;
    } c1 = c2;
    c2 += bisint;
    if (c2 > maxv)
      done = 1;
  }
  return nroots;
}
```

```
/* keeps all roots */ getallvs(k,h, params,r, vels, bisint, vacc, maxroots)
double k, bisint, vacc;
vector h,params, vels,r;
int maxroots;
{
  double c2, c1, lastroot=0.0, root, frtbis(), maxv;
  int nroots=0, done=0;

maxv=10000.0;
  c1=100.1;

c2 = c1 + bisint;
  while(!done){
     if( ((root=frtbis(k,h,params,r,c1,c2,vacc))>SMALL)
            && fabs(root-lastroot)>vacc ){
       vels[nroots] = root;
       lastroot = root;
       nroots++;
       if(nroots == maxroots)
          done = 1;
     } c1 = c2;
     c2 += bisint;
     if (c2 > maxv)
        done = 1;
  }
  return nroots;
} define JMAX 40 double frtbis(k,h,pa,r,v1,v2,vacc)
double k, v1,v2,vacc;
```

17

```
vector h,pa,r;
{
    int j;
    double dv, f, fmid, vmid, rtb, z[2], funceval();

if(!z){
      fprintf(stderr,"no memory in frtbis\n");
      exit(-1);
    } z[1] = k;

z[0] = v1;
    f=funceval(z,h,pa,r);

z[0] = v2;
    fmid=funceval(z,h,pa,r);

if (f*fmid >= 0.0) return (0.0);

rtb = f < 0.0 ? (dv=v2-v1,v1) : (dv=v1-v2,v2);
    for (j=1;j<=JMAX;j++) {
          vmid = rtb+(dv *= 0.5);
          z[0] = vmid;
          fmid=funceval(z,h,pa,r);
/*        if (fmid==NULL){
             vfree(z);
             return(0.0);} */
          if (fmid <= 0.0) rtb=vmid;
          if (fabs(dv) < vacc || fmid == 0.0) return rtb;
    }
    fprintf(stderr, "Too many bisections in FRTBIS\n");

return (0.0);
} undef JMAX
```

```
/* -h<y<0 is film,  y>0 is substrate */ getdispl(potents, vs, y, clgf, ctrf, k, uy, uz, numvs)
comatrix potents;
vector vs;
covector uy, uz;
double clgf, ctrf, k,y;
{
  int i;
  complex ik;
  covector a, b, c, d;
  covector o, p;

a = covdim(numvs);
  b = covdim(numvs);
  c = covdim(numvs);
  d = covdim(numvs);
  o = covdim(numvs);
  p = covdim(numvs);
  if(!p){
    fprintf(stderr,"no memory\n");
    exit(-1);
  } ik = Complex(0.0,k);
  if (y<0.0){
    for(i=0; i<numvs; i++){
      o[i] = Csqrt(Complex(1 - vs[i]*vs[i]/(clgf*clgf),0));
      p[i] = Csqrt(Complex(1 - vs[i]*vs[i]/(ctrf*ctrf),0));
      a[i] = Cmul(potents[i][0],Cexp(RCmul(k*y,o[i])));
      b[i] = Cmul(potents[i][1],Cexp(RCmul(-k*y,o[i])));
      c[i] = Cmul(potents[i][2],Cexp(RCmul(k*y,p[i])));
      d[i] = Cmul(potents[i][3],Cexp(RCmul(-k*y,p[i])));
    }
  }
  else{
    for(i=0; i<numvs; i++){
      o[i] = Csqrt(Complex(1 - vs[i]*vs[i]/(clgf*clgf),0));
```

```
    p[i] = Csqrt(Complex(1 - vs[i]*vs[i]/(ctrf*ctrf),0));
    a[i].re = 0.0;
    a[i].im = 0.0;
    b[i] = Cmul(potents[i][4],Cexp(RCmul(-k*y,o[i])));
    c[i].re = 0.0;
    c[i].im = 0.0;
    d[i] = Cmul(potents[i][5],Cexp(RCmul(-k*y,p[i])));
   }
 } for(i=0; i<numvs; i++){
  uy[i] = Cadd(Cmul(RCmul(k,o[i]),Csub(a[i],b[i])),
            Cmul(ik,Cadd(c[i],d[i])));
  uz[i] = Cadd(Cmul(RCmul(k,p[i]),Csub(d[i],c[i])),
            Cmul(ik,Cadd(a[i],b[i])));
 }
 cvfree(a);
 cvfree(b);
 cvfree(c);
 cvfree(d);
 cvfree(o);
 cvfree(p);

} getlgtrdispl(potents, vs, y, clgf, ctrf, k, uyl, uzl, uyt, uzt, numvs)
comatrix potents;
vector vs;
covector uyl, uzl, uyt, uzt;
double clgf, ctrf, k,y;
{
 int i;
 complex ik;
 covector a, b, c, d;
 covector o, p;

a = covdim(numvs);
 b = covdim(numvs);
 c = covdim(numvs);
```

```
d = covdim(numvs);
o = covdim(numvs);
p = covdim(numvs);
if(!p){
  fprintf(stderr,"no memory\n");
  exit(-1);
} ik = Complex(0.0,k);
if (y>0.0){
  for(i=0; i<numvs; i++){
    o[i] = Csqrt(Complex(1 - vs[i]*vs[i]/(clgf*clgf),0));
    p[i] = Csqrt(Complex(1 - vs[i]*vs[i]/(ctrf*ctrf),0));
    a[i] = Cmul(potents[i][0],Cexp(RCmul(-k*y,o[i])));
    b[i] = Cmul(potents[i][1],Cexp(RCmul(k*y,o[i])));
    c[i] = Cmul(potents[i][2],Cexp(RCmul(-k*y,p[i])));
    d[i] = Cmul(potents[i][3],Cexp(RCmul(k*y,p[i])));
  }
}
else{
  for(i=0; i<numvs; i++){
    o[i] = Csqrt(Complex(1 - vs[i]*vs[i]/(clgf*clgf),0));
    p[i] = Csqrt(Complex(1 - vs[i]*vs[i]/(ctrf*ctrf),0));
    a[i].re = 0.0;
    a[i].im = 0.0;
    b[i] = Cmul(potents[i][4],Cexp(RCmul(k*y,o[i])));
    c[i].re = 0.0;
    c[i].im = 0.0;
    d[i] = Cmul(potents[i][5],Cexp(RCmul(k*y,p[i])));
  }
} for(i=0; i<numvs; i++){
  uyl[i] = Cmul(RCmul(k,o[i]),Csub(a[i],b[i]));
  uzl[i] = Cmul(ik,Cadd(a[i],b[i]));
  uyt[i] = Cmul(ik,Cadd(c[i],d[i]));
  uzt[i] = Cmul(RCmul(k,p[i]),Csub(d[i],c[i]));
}
cvfree(a);
cvfree(b);
```

```
        cvfree(c);
        cvfree(d);
        cvfree(o);
        cvfree(p);

}
```

What is claimed is:

1. A method for determining the anisotropy between an out-of-plane and an in-plane material property of a thin sample, wherein an exposed surface of said thin sample extends substantially along said plane, comprising:

exciting time-dependent waveguide acoustic modes in the sample by directing two time-coincident laser pulses onto the sample so that they overlap in an excitation region and interfere to form an excitation field having a known wavevector, detecting said waveguide acoustic modes by directing a probe beam onto the excitation region so that it is diffracted, said probe beam having a temporal width that is comparable to the detectable presence of said waveguide acoustic modes;

analyzing the diffracted probe beam to measure phase velocities of said waveguide acoustic modes, and determining the anisotropy between the out-of-plane and the in-plane mechanical property of said sample by:

proposing stiffness tensors in directions of interest, calculating phase velocities based on said proposed stiffness tensors, comparing said calculated phase velocities to said measured phase velocities, repeating said proposing, calculating, and comparing until said calculated phase velocities match said measured phase velocities to a desired degree, and determining the anisotropy between the out-of-plane and the in-plane mechanical property in the direction of interest from the stiffness tensors for which the calculated phase velocities match the measured phase velocities to said desired degree.

2. The method of claim 1 wherein said probe beam has a small dimension compared to said excitation region and the equations of motion for said sample are described by $$\rho \frac{\partial^2 u_i}{\partial t^2} - c_{ijkl} \frac{\partial^2 u_k}{\partial x_j \partial x_l} = 0$$

where $\rho$ is the density, $\mu$ is the displacement, c is the stiffness tensor, and the coordinate system is defined with the wavevector in the z direction.

3. The method of claim 2 wherein said excitation pulses are cylindrically focused to form an elliptical spot with the major axis of said elliptical spot being in the z direction.

4. The method of claim 2 wherein the probe pulse has a dimension of about an order of magnitude smaller than said excitation region.

5. The method of claim 1, wherein said laser pulses are selected to maximize the number of waveguide modes excited in said sample by having a wavelength at which the sample is about 20–80% absorbant.

6. The method of claim 1 wherein the wavevector-thickness product is between about 2–6.

7. The method of claim 1, wherein said probe beam is generated by temporally modulating an output of a cw laser.

8. The method of claim 7, wherein said probe beam has a square temporal profile.

9. The method of claim 1 further comprising comparing the determined anisotropic material properties of the thin sample with at least one previously determined property to allow the quality of the film to be monitored.

10. The method of claim 9, wherein the anisotropic property is a sound velocity.

11. A method for determining the anisotropy between an out-of-plane and an in-plane mechanical property of a thin sample, wherein an exposed surface of said thin sample extends substantially along said plane, comprising:

exciting time-dependent waveguide acoustic modes in the sample by directing two time-coincident laser pulses onto the sample so that they overlap in an excitation region and interfere to form an excitation field having a known wavevector, detecting said waveguide acoustic modes by directing a probe beam onto the excitation region so that it is diffracted, said probe beam having a temporal width that is comparable to the detectable presence of said waveguide acoustic mode;

measuring a phase velocity or frequency of said waveguide acoustic modes from said diffracted probe beam; and analyzing the phase velocity or frequency of said acoustic waveguide modes to determine the anisotropy between the out-of-plane and the in-plane mechanical property of said sample.

12. A method for determining an out-of-plane mechanical property of a thin sample, comprising:

exciting time-dependent waveguide acoustic modes in the sample by directing two time-coincident laser pulses onto the sample so that they overlap in an excitation region and interfere to form an excitation field having a known wavevector;

detecting the waveguide acoustic modes by directing a probe beam onto the excitation region so that it is diffracted, with the probe beam having a temporal width that is comparable to the detectable presence of the waveguide acoustic modes;

measuring a phase velocity or frequency of the waveguide acoustic modes from the diffracted probe beam; and analyzing the phase velocity or frequency of the waveguide acoustic modes to determine the out-of-plane mechanical property of the sample.

13. The method of claim 12, wherein the waveguide acoustic modes compress and expand the thin sample along its thickness.

14. The method of claim 13, wherein the out-of-plane mechanical property is calculated along the thickness of the thin sample.

15. The method of claim 14, wherein the mechanical property is the stiffness or elastic moduli of the thin sample.

16. The method of claim 12, wherein during said determining an anisotropy between the out-of-plane mechanical property and an in-plane mechanical property is determined.

17. The method of claim 11, wherein the waveguide acoustic modes compress and expand the thin sample along its thickness.

18. The method of claim 17, wherein the mechanical property is the stiffness of the thin sample.

* * * * *